United States Patent [19]

Raymond et al.

[11] Patent Number: 5,892,029
[45] Date of Patent: Apr. 6, 1999

[54] 3-HYDROXY-2(1H)-PYRIDINONE CHELATING AGENTS

[75] Inventors: Kenneth Raymond; Jide Xu, both of Berkeley, Calif.

[73] Assignee: The Regents of the University of California, Oakland, Calif.

[21] Appl. No.: 837,729

[22] Filed: Apr. 22, 1997

Related U.S. Application Data

[60] Division of Ser. No. 285,640, Aug. 2, 1994, Pat. No. 5,624,901, which is a continuation-in-part of Ser. No. 227,969, Apr. 15, 1994, abandoned.

[51] Int. Cl.⁶ ...................... C07D 401/12; C07D 405/12; C07D 403/12
[52] U.S. Cl. .............................. 540/474; 546/6; 546/256; 546/268.1; 546/296
[58] Field of Search ........................... 546/6, 256, 268.1, 546/296; 514/183, 184, 348, 350; 540/474

[56] References Cited

U.S. PATENT DOCUMENTS 4,698,431  10/1987  Raymond et al. ...................... 546/298
5,624,901   4/1997  Raymond et al. ........................ 514/17

*Primary Examiner*—Alan L. Rotman
*Attorney, Agent, or Firm*—Townsend and Townsend and Crew LLP

[57] ABSTRACT

Disclosed is a series of improved chelating agents and the chelates formed from these agents, which are highly effective upon both injection and oral administration. Several of the most effective are of low toxicity. These chelating agents incorporate within their structure 3-hydroxy-2-pyridinone (3,2-HOPO) moieties with a substituted carbamoyl group ortho to the hydroxy group of the hydroxypyridinone ring. The electron-withdrawing carbamoyl group increases the acidity, as well as the chemical stability towards oxidation and reduction, of the hydroxypyridinones. In the metal complexes of the chelating agents, the amide protons form very strong hydrogen bonds with the adjacent HOPO oxygen donor, making these complexes very stable at physiological conditions. The terminal N-substituents provide a certain degree of lipophilicity to the 3,2-HOPO, increasing oral activity.

2 Claims, 2 Drawing Sheets

3-HYDROXY-2(1H)-PYRIDINONE CHELATING AGENTS

CROSS REFERENCE TO RELATED APPLICATIONS

This application is a division and continuation-in-part of application Ser. No. 08/285,640, filed Aug. 2, 1994, now U.S. Pat. No. 5,624,901, which was a continuation-in-part of application Ser. No. 08/227,969, filed Apr. 13, 1994, now abandoned. The disclosures of both applications Ser. No. 08/285,640 and Ser. No. 08/227,969 are incorporated herein by reference.

GOVERNMENT RIGHTS

The Government has rights in this invention pursuant to Contract No. DE-AC03-76SF00098 awarded by the U.S. Department of Energy (DOE). The uranium and plutonium chemistry is supported through the DOE. The iron chemistry is supported on the Berkeley campus of the University of California by NIH grants AI 11744 and DK 32999. The plutonium decorporation and ligand toxicology are supported by NIEHS grant ES 02698.

BACKGROUND OF THE INVENTION

1. Field of the Invention

The present invention relates generally to improved therapeutic metal chelating agents which are highly effective and have low toxicity upon injected and oral administration, and in particular to chelating agents which incorporate within their structures 3-hydroxy-2-pyridinone (3,2-HOPO) moieties with a carbamoyl group substituted on the ring carbon atom ortho to the hydroxy or oxo group of the HOPO ring.

2. Description of Related Art Including Information Disclosed Under §§ 1.97–1.99

Siderophores are highly selective and effective ferric chelating agents synthesized and released by microorganisms to ensure the presence of sufficient iron in solubilized form for cell reproduction. It was recognized early on that the affinity and selectivity of the siderophores for ferric ion made these compounds good candidates for therapeutic iron removal agents. This is particularly true for patients who suffer from blood diseases such as beta thalassemia, the treatment of which requires the regular transfusion of whole blood and results in the accumulation of massive tissue iron deposits. Because of the similarity in coordination properties between Fe(III) and tetravalent actinides, tetravalent actinides have great affinity for electron-donor groups that bind Fe(III), and follow Fe(III) in mammalian iron transport and storage systems. The great affinity and specificity of the siderophores towards Fe(III) suggest that modification of siderophores, which are effective sequestering agents for ferric ion, would yield potential chelators of tetravalent actinides, which present significant biological hazards associated with nuclear technology. Following absorption, the actinide cations that have been inhaled, ingested, or deposited in a wound circulate in serum bound to transferrin (Tf), the iron transport protein, and renal and gastrointestinal excretion are severely inhibited. As actinide-containing cells and structures die, the released actinide is recirculated, and nearly all of it is re-deposited at new sites. The alpha particles emitted by the actinides kill cells and induce cancer in the major storage tissues—lung, bone, liver. The only known way to reduce the toxicity of these radioactive metals is to use chelating agents to accelerate their excretion, thereby preventing deposition or re-deposition. Normally, such actinide chelating agents will be octadentate ligands, as opposed to the generally hexadentate or tetradentate siderophores. Other uses, such as radionuclide chelation in nuclear medicine applications, for example, are also clearly possible.

The biomimetic approach of the present invention, which designs and synthesizes sequestering agents for ferric ion and actinides, is based on siderophores. The metal binding units of siderophores are usually either catechols (dihydroxybenzene analogs; Formula 1A) or hydroxamic acids (Formula 1B):

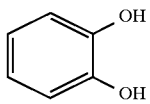

Formula 1A

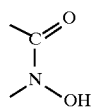

Formula 1B

In fact, desferrioxamine B (DFO), a tri-hydroxamic acid siderophore, is used as a human iron sequestering agent. This chelating agent has predominated for over 30 years as the method of choice for treatment of iron overload. However, DFO has low oral activity and a number of adverse effects: including administration via a cumbersome subcutaneous infusion, leading to poor patient compliance with the treatment regime, and poor efficacy in removing deposited actinides. As a result of these limitations of the prior art drugs, there is a need for more effective and orally active iron sequestering agents to treat iron overload as well as actinide poisoning.

The most potent natural Fe(III) chelator is enterobactin, a siderophore produced by enteric bacteria with a formation constant of $K_f \approx 10^{49}$, pM=35.5. This hexadentate ligand is composed of three catechoylamide groups attached to a tri-serine lactone backbone. Catecholates are much stronger sequestering agents than hydroxamate ligands, such as DFO, and these ligands are faster in removing iron from human transferrin, primarily for kinetic rather than thermodynamic reasons. Synthetic analogues of catechol-based siderophores are also known. However, there are a number of difficulties in developing catecholates into effective pharmaceutical agents. A number of catecholate siderophores, including enterobactin, will be bound by albumin in serum. They also strongly promote the growth of pathogenic microorganisms. The weak acidity of catechol and the required loss of two protons per catechol group at or about neutral pH limit the effectiveness of catechol-based ligands in vivo. These factors place severe limitations on the use of catechol-based ligands as therapeutic agents. It is therefore desirable to provide a medicinally useful metal chelating agent having a higher $K_a$, i.e., more acidic, and which therefore binds more effectively at physiological pH, than catechol-based compounds. Uninegative ligands, i.e., ligands having a single negative charge near neutral pH range, are particularly desirable, in contrast to the correspondingly highly charged ferric and plutonium catechol complexes.

Derivatives of hydroxypyridinones ("HOPO") are of particular interest, since these ligands selectively display high affinity for ferric and actinide ion. These ligands and their mono-anions have a zwitterionic resonance form that is isoelectronic with the catechol dianion. The abbreviation "HOPO" will hereinafter be used to include hydroxypyridinone analogs as well as isomers or tautomers thereof, in either protonated or deprotonated forms.

The HOPO ligands have been shown to be very promising sequestering agents. The bidentate 3,4-HOPO ligand, 1,2-dimethyl-3-hydroxy-4-pyridinone, is orally active and has gone through extensive study, including clinical trials. However, there are many limitations for such a simple bidentate ligand. Multidentate HOPO derivatives have advantages over simpler bidentate ligands: in particular, low toxicity resulting from a higher binding affinity (pM) at low (clinical level) ligand concentrations.

Previous patents on hydroxypyridone ligands used as chelating agents include "Hydroxypyridonate Chelating Agents", U.S. Pat. No. 4,698,431, patented by Kenneth N. Raymond, Robert C. Scarrow, and David L. White, Oct. 6, 1987. This invention provided 1,2-HOPO derivatives with either an amide or a carboxylic acid moiety in the number 6 position. These chelating agents are useful in selectively removing certain cations from solution and are particularly useful as ferric ion and actinide chelators. However, U.S. Pat. No. 4,698,431 did not claim other chelating agents having 3,2-HOPO moieties incorporated within their structures or a carboxy moiety on the number 3 position of 1,2-HOPO ring.

Other related art includes Pharmaceutical Compositions of Hydroxypyridones, U.S. Pat. No. 4,666,927, patented by Robert C. Hider, George Kontoghiorghes, Jack Silver, and Michael A. Stockham, May 19, 1987. Claim 1 of this patent claims a number of possible chelating agents having 1,2-HOPO, 3,2-HOPO, or 3,4-HOPO moieties incorporated within their structures that are linked through a number of possible combinations of linking groups, including —CONH— groups. However, U.S. Pat. No. 4,666,927 teaches against a HOPO moiety having a substitution ortho to the hydroxy or oxo group of the HOPO ring.

In contrast to U.S. Pat. No. 4,666,927, the inventors have developed a new design strategy, that is to synthesize a new series of 3,2-HOPO derivatives with either a carboxylic acid or a (substituted) carbamoyl moiety substituted on the ring carbon ortho to the HOPO hydroxy group. The particular coordination geometry and the hydrogen bonding between the amide proton and HOPO oxygen donor in these HOPO-metal complexes disclosed by the present invention thereby make the new series of 3,2-HOPO derivatives unusually good complexing agents having very high stability and specificity towards metal binding. The inventors further found these new compounds have stronger acidity and chelating ability for iron and actinides and have high oral activity in removing toxic actinides in vivo.

Furthermore, the method of synthesizing the present invention having 3,2-HOPO moieties incorporated within their structures with the (substituted) carbamoyl group ortho to hydroxy group of HOPO ring is not obvious. One earlier attempt by the inventors included: reacting 4-carboxy-3-hydroxy-2(1H)-pyridinones (Formula 9A) with 1,1'-carbonyldiimidizole to produce the active amide intermediate, which is then combined with backbone amines to form the corresponding novel 3,2-HOPO ligands, similar to the case of thiohydroxamate. See, e.g., Kamal Abu-Dari and Kenneth N. Raymond, "Ferric Ion Sequestering Agents. 23. Synthesis of Tris(hydroxypyridinethione) Ligands and Their Ferric Complexes; X-ray Structure Analysis of N,N',N"-Tris(((1,2-didehydro-1-hydroxy-2-thioxopyrid-6-yl) carbonyl)-2,2',2"-triaminotriethylaminato)iron(III),"  *Inorg. Chem.* 1991, 30, 519–524. However, the purification of the final product is difficult, therefore, this method is not preferred. A second attempt to carry out the above reaction produced the acid chloride of 1-alkyl-4-carboxy-3-hydroxy-2(1H)-pyridinone as an active intermediate using thionyl chloride or oxalyl chloride, similar to the case of catechoylamide ligands. Due to the low yield of compound in preliminary tests, this method is also not preferred.

The present invention discloses a process to synthesize the desired multidentate 3,2-HOPO ligand in good yield.

Accordingly the present invention comprises an effective multidentate siderophore analog HOPO ligand in which one or more HOPO rings are linked to a molecular or a polymeric backbone through amide linkages. The inventors have previously reported the synthesis of siderophore analogs with linear, multipedal and macrocyclic topologies, and have shown a more effective ligand is one with a greater predisposition toward binding. In the design of the present invention, these synthetic strategies, as well as the binding abilities, solubility and lipophilicity of the resulted compounds, are important factors considered.

SUMMARY OF THE INVENTION

Figure 1:
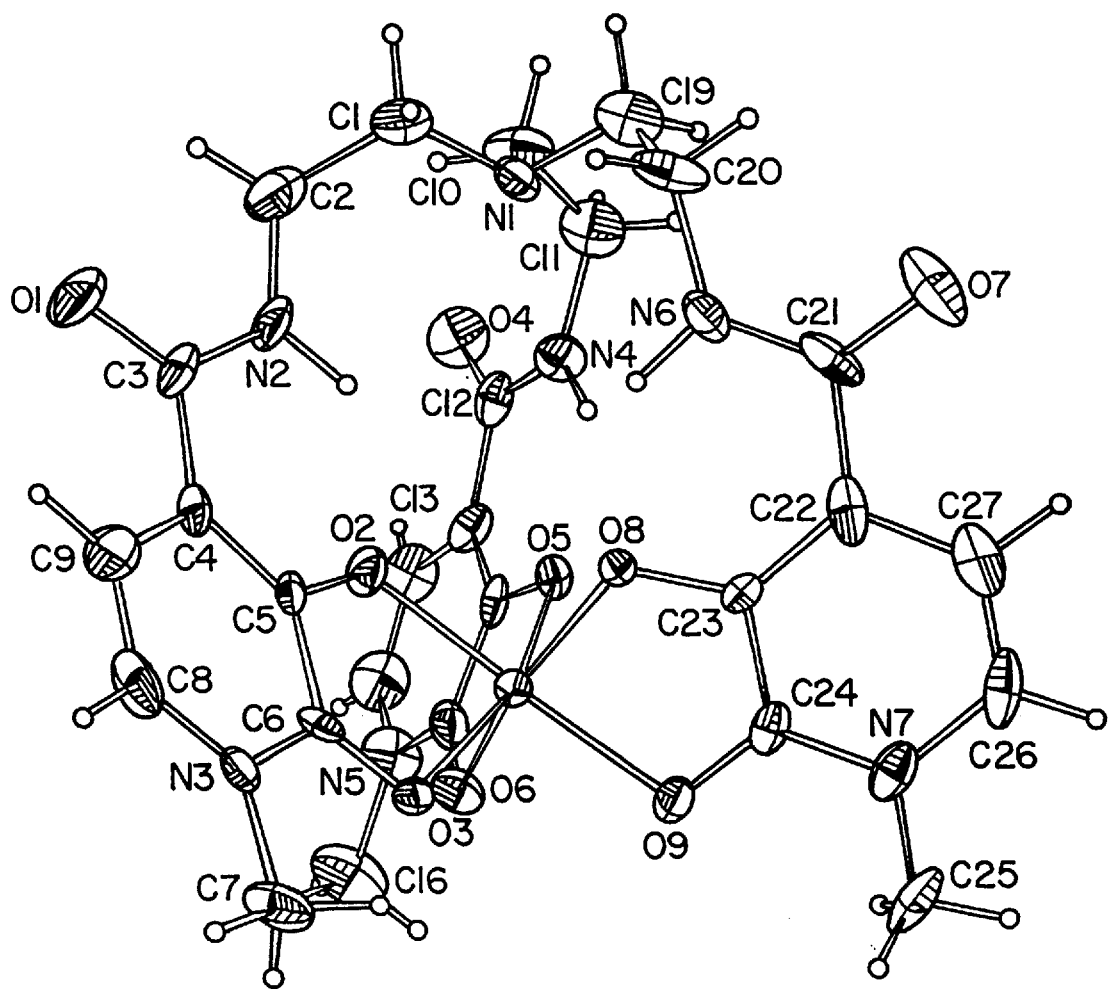
FIG. 1 is a diagram showing the crystal structure of the Fe(III)-TREN-3,2 HOPO complex.

The present invention represents a breakthrough in siderophore-like ligands intended for pharmaceutical use. The present invention provides novel 1,2-HOPO and 3,2-HOPO chelating agents capable of selectively forming stable complexes with certain cations such as $Fe^{3+}$, $Gd^{3+}$, $Am^{3+}$, $Pu^{4+}$, $Np^{4+}$, and $U^{6+}$ ions.

The present invention allows this highly advantageous class of chemicals to be administered orally or by injection.

These complexing agents are lipophilic enough to display oral activity.

The present invention provides a method to produce these compounds safely and in good yield.

The present invention provides unusually good complexing agents with high stability and specificity for iron and actinides.

The present invention provides chelating agents which are relatively acidic and incorporate monoprotic ligand groups.

The present invention provides methods of using the novel chelating agents.

The present invention provides methods of synthesizing the novel chelating agents. These new HOPO ligands are generally synthesized by introducing a carboxylate group at the carbon atom ortho to the ligating group of HOPO ring, then making an amide linkage to a suitable molecular backbone.

In one aspect of the invention, novel chelating agents are provided which include HOPO-based bidentate and multidentate ligands, as well as mixed multidentate ligands such as HOPO-substituted desferrioxamine. In other aspects of the invention, novel methods of synthesizing the HOPO-derived chelating agents are provided, as are methods of using the novel compounds.

DETAILED DESCRIPTION OF THE INVENTION

The present invention provides novel 3,2-HOPO chelating agents capable of selectively forming stable complexes with certain cations such as $Fe^{3+}$, $Gd^{3+}$, $Am^{3+}$ and $Pu^{4+}$, $Np^{4+}$, and $U^{6+}$ ions. Accordingly the present invention comprises a compound consisting of 4-(substituted)

carbamoyl-3-hydroxy-2-pyridinones having optional substituents on the nitrogen atom, and on one or more of the carbon atoms of the ring. Shown below are the preferred basic ring system in the compounds of the present invention (Formula 2), the basic ring system of 1,2-HOPO-6-carbamoylamide (Formula 3), and catechoylamide (Formula 4):

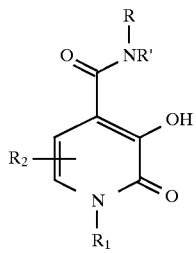

Formula 2

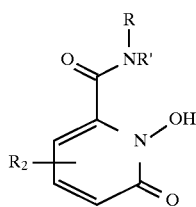

Formula 3

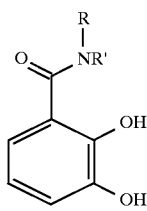

Formula 4 wherein $R_1$ and $R_2$ are separately selected from the group consisting of: hydrogen, $C_1$–$C_4$ aliphatic hydrocarbon groups, and $C_1$–$C_4$ aliphatic hydrocarbon groups substituted by a single halide, hydroxy, or carboxy group or an aryl group.

The HOPO rings are attached to a molecular or polymeric backbone R through amide linkages, where R is selected from multi-linking groups. Representative examples of such multi-linking groups include, but are not limited to:

Formula 5A
(m = 1–3, n = 1–3, p = 1–3)

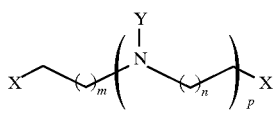

Formula 5B
(m = 1–3, n = 1–3, p = 1–3)

Formula 5C
(q = 1–6)

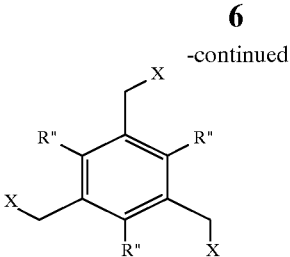

Formula 5D
(R" = H, alkyl)

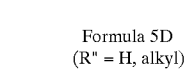

Formula 5E
(r = 1, 2)

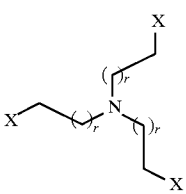

Formula 5F

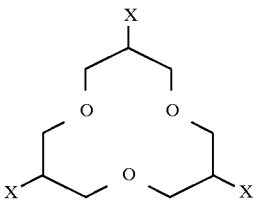

Formula 5G
(s = 1–2)

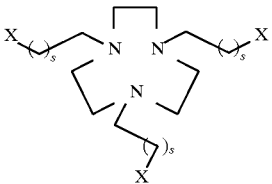

Formula 5H
(t = 2–6, u = 2–4)

wherein the several X's of a formula may be a combination of chelating agents selected from the group consisting of:

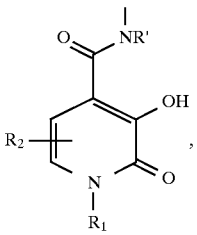

,

-continued

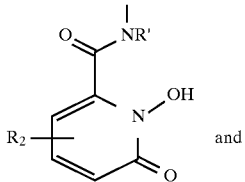

and

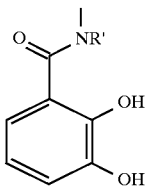

and Y is a 3,2-HOPO or 1,2-HOPO structural unit selected from the group consisting of:

Formula 5L

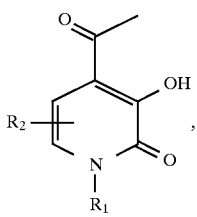

Formula 5M

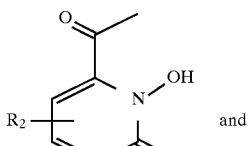

and

Formula 5N

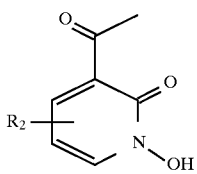

where the free valency in each case indicates the preferred attachment point of the chelating group to a backbone.

In Formulas 5A to 5H, some of the chelating units X and Y may also be substituted by other chelating structural units. Representative examples of other chelating units include, but are not limited to: aminoacetic acid, hydroxamic acid, catechol, 2,3-dihydroxyterephthalamide or 3,4-HOPO.

Due to the presence of electron-withdrawing substituted carbamoyl group ortho to the hydroxy group of HOPO ring, compounds of Formulas 3 and 4 have lower $pK_a$s and more preferable coordination properties than corresponding HOPO ligands without the carbamoyl substituents. Their ring systems are also more able to withstand reduction or oxidation than corresponding HOPO ligands without the carbamoyl substituents. Similar to the case of catechoylamide complexes (Formula 6) and 1,2-HOPO-6-ylamide complexes (Formula 7), the strong hydrogen bonding between the amide proton and the adjacent oxygen donor, the hydroxy oxygen atom, also enhances the stability of the 3,2-HOPO complexes of this invention (Formula 8) as shown below:

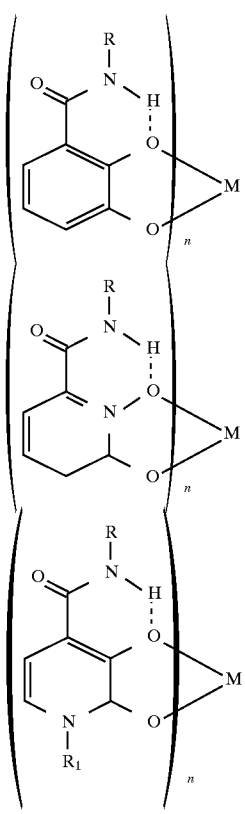

Formula 6

Formula 7

Formula 8 wherein M is a metal ion with a high charge to radius ratio and R in each case is a molecular or polymeric backbone.

These chelating agents become very powerful chelators of metal ions with high charge to radius ratios.

Another important feature of the 3,2-HOPO ligands of this invention is that these compounds have a terminal $R_1$ group substituted on the HOPO ring nitrogen, which provides certain adjustable lipophilicity to the whole molecule, necessary for the ligand to display oral activity.

The lipophilic properties of the HOPO substituted compounds in combination with their relatively low $pK_a$s make them effective oral agents, a highly desirable property for therapeutic agents. The new 3,2-HOPO compounds display high binding constants for ferric ion, on the order of $10^{26}$ to $10^{29}$ $M^{-3}$, and pM values from 19 to 27 for the Fe(III)-tris (HOPO) complexes and are thus effective ligands for iron as well as for certain other ions with similar coordination properties (e.g., the actinide(IV) ions). These ligands are also surprisingly good chelating agents for the lanthanides.

Monomeric bidentate compounds of the invention include those given by the structure of Formula 9A, 9B and 9C.

Formula 9A

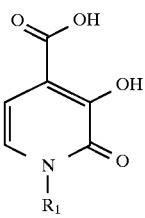

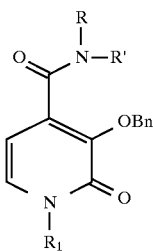

Formula 9B

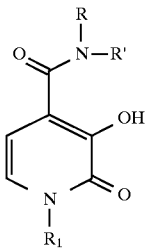

Formula 9C

Formula 9A shows the acid form, while Formulas 9B and 9C show the benzyl protected amide form and deprotected amide form respectively. In these forms, R is a molecular or polymeric backbone, and $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group. When $R_1$ is selected from these groups, the molecule is provided with adjustable lipophilicity. In Formula 9B and 9C, R' is selected from the group consisting of: hydrogen, $C_{1-8}$ aliphatic hydrocarbon groups, and $C_{1-8}$ aliphatic hydrocarbon groups substituted by a single carboxy, sulpho, sulphamoyl, N-methyl or N-ethyl sulphamoyl group, or an aryl group. Optionally, formulas 9A and 9C are in the form of a physiologically acceptable salt.

The new HOPO monomers display high affinity for ferric ions. For example, 1-methyl-4(1-propylcarbamoyl)-3-hydroxy-2(1H)-pyridinone (Formula 9C, backbone=n-propyl, R'=H, $R_1$=methyl) has overall complex binding constants on the order of $10^{28.7}$ M-3 for Fe(III). However, because of the 3:1 stoichiometry of the bidentate monomer/Fe complex, its stability is strongly dependent on its concentration (by the 3rd power). Generally, the pM concept was used to define the concentration of unchelated metal ion at physiological pH (7.4), and at chelator and metal ion concentrations (10 and 1 $\mu$M, respectively) which are those expected in the plasma of a chelator-treated patient. The more effective chelator has the larger pM value. Since the multidentate 3,2-HOPO ligands have higher pM values than their bidentate analogs, they have stronger scavenging power for iron and actinides in vivo. For example, the bidentate compound 1-methyl-4(1-propylcarbamoyl)-3-hydroxy-2(1H)-pyridinone has a pM of 19.26 for Fe(III), while the hexadentate compound TREN-Me-3,2-HOPO (Formula 12, m=1) has a pM of 26.69 for Fe(III).

Tetradentate chelating agents of the present invention, which incorporate two 3,2-HOPO structural units, are given by Formula 10. These compounds form stable 2:1 complexes with actinides, and are promising actinide sequestering agents.

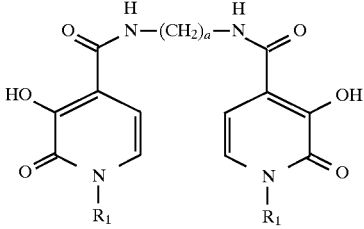

Formula 10

In Formula 10, two 3,2-HOPO structural units are linked to an aliphatic hydrocarbon molecular backbone—$(CH_2)_a$—, $R_1$ is as given above for the monomers of Formula 9, and a is an integer from 2 to 9. In a particularly preferred form, a is five, and the structure is "5-LI-Me-3,2-HOPO" (1-Methyl-3-hydroxy-2(1H)-pyridinone structures separated by five methylene groups, somewhat analogous in structure to previously known 5-LICAM, i.e. linear catechoylamide sequestering agents). Alternative molecular backbones of special interest are groups corresponding to a hydrocarbon group in which one or more $CH_2$ groups are replaced by one or more oxygen or nitrogen atoms. Such backbones are preferably more hydrophilic and the corresponding ligands will have better solubility in water. Specific examples of such tetradentate ligands are given by Formula 11, in which $R_1$ is as given above for the

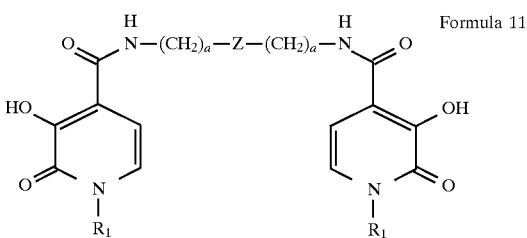

Formula 11 monomers of Formula 9, and a and b are each an integer from 2 to 4, and Z may be oxygen or nitrogen (with a hydrogen, alkyl or aryl substitution).

Since hexadentate chelating agents form 1:1 complexes with iron, their stability has first order dependence on the ligand concentration. In other words, the hexadentate 3,2-HOPO ligands have strong scavenging power for iron at low concentration of ligand. The inventors note that the new tetradentate and hexadentate 3,2-HOPO ligands are not only excellent iron sequestering agents but also excellent actinide sequestering agents in vivo. This is surprising because actinides have coordination numbers greater than eight and therefore would not be expected to bind well to tetradentate or hexadentate chelating agents. This is not the case for tetradentate CAM or 1,2-HOPO sequestering agents, which are less effective in vivo.

Furthermore, because the new HOPOs are such effective chelators, it is possible that they can be used as MRI diagnosis complexing agents. As a specific example, see example 20, infra.

Hexadentate chelating agents of the present invention which incorporate three 3,2-HOPO structural units with a tripodal amine backbone are given by Formula 12 and 13. In both Formulas, $R_1$ is as given above for the monomers of Formula 9; and in Formula 12, m is an integer from 1 to 3.

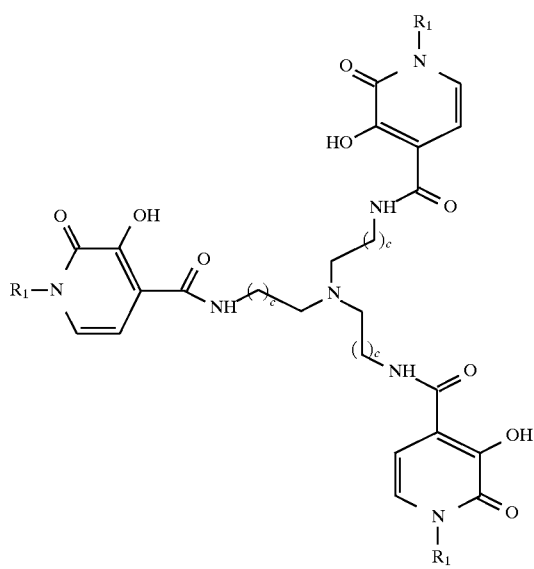

Formula 12

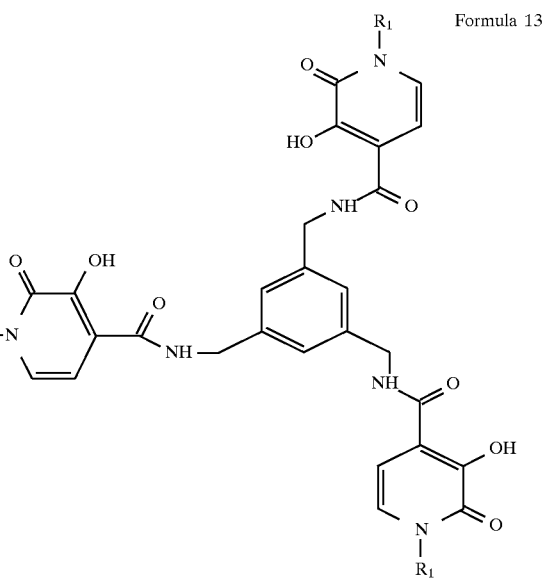

Formula 13

The compound of Formula 12 with c=1 represents a particularly preferred embodiment of the invention, as it has been demonstrated to be non-toxic and extremely effective both in ferric chelation and in the decorporation of actinides such as Pu(IV), Am(III) and U(VI). This structure is abbreviated as TREN-Me-3,2-HOPO, similar in structure to previously known triscatechoylamide ligand TRENCAM.

Octadentate chelating agents provided by the present invention which incorporate four 3,2-HOPO structural units are given by Formula 14. This design is based on the siderophore analogs with 'H' shaped tetrapodal topology developed by the inventors, which proved to be predisposed towards metal binding. These chelating agents are specially suitable for binding actinide (IV) ions, because of their preferred high coordination number (eight or greater).

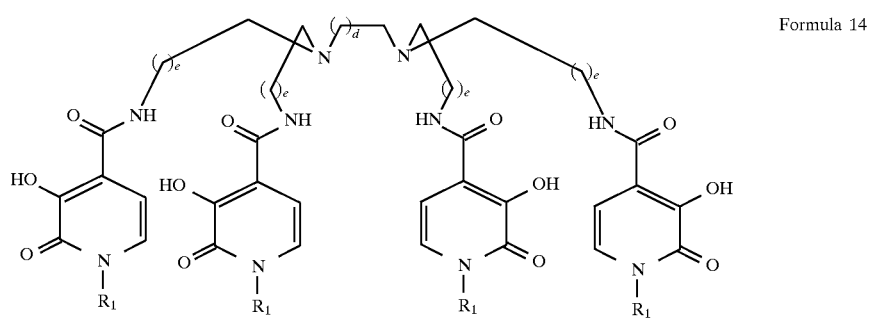

Formula 14

In Formula 14, $R_1$ is as given above for the monomers of Formula 9, and d and e are each an integer from 1 to 4.

The chelating agents of this invention also include mixed HOPO ligands which in addition to having at least one 3,2-HOPO structural unit, may also have other chelating structural units. Examples of these mixed chelating agents are given by Formulas 15–17.

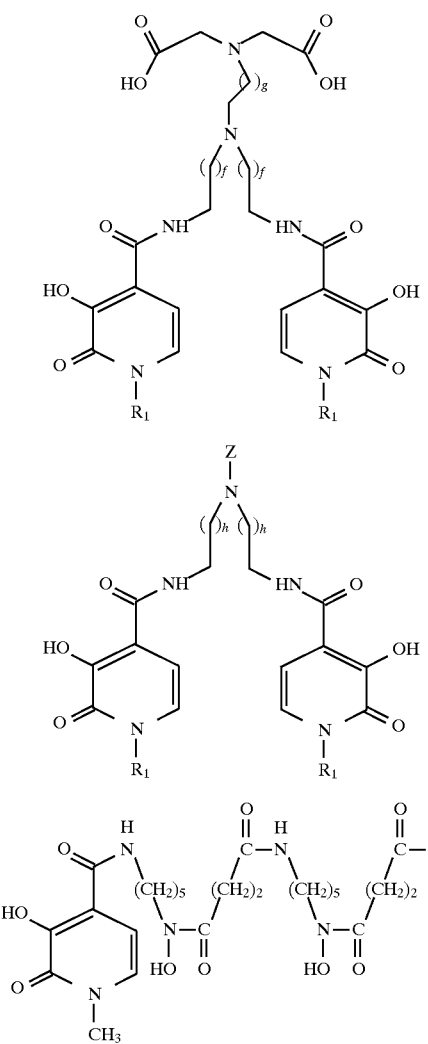

Formula 15

Formula 16

Formula 17

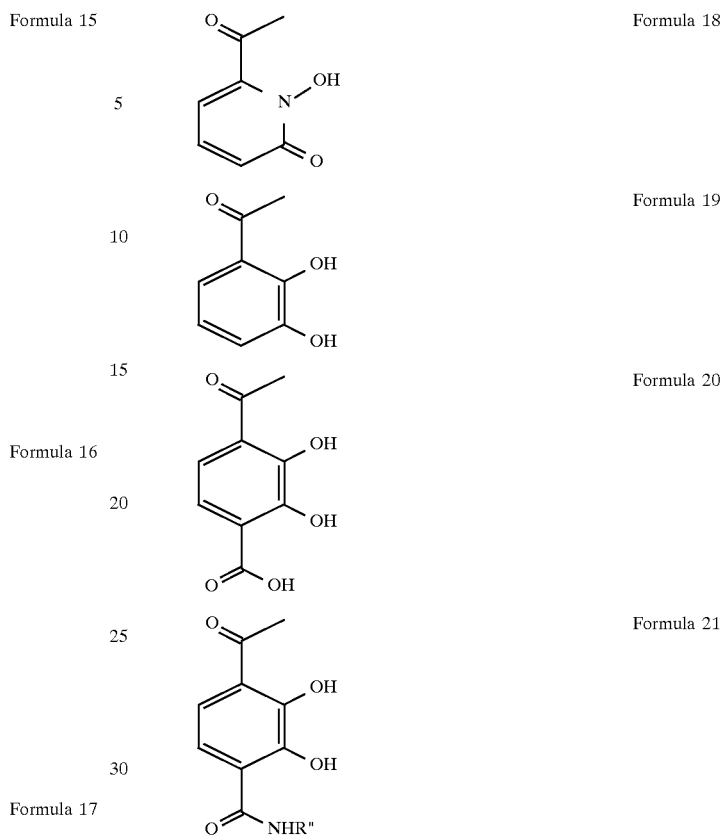

Formula 18

Formula 19

Formula 20

Formula 21

Formula 15 gives a 3,2-HOPO-substituted analog of ethylenediamine-N,N,N', N'-tetraacetic acid (EDTA) and Formula 16 gives a 3,2-HOPO substituted diethylenetriamine analog with the Z moiety which is selected from the group consisting of: hydrogen, $C_{1-40}$ hydrocarbon groups, 2-hydroxyethyl, 2-aminoethyl, and $C_{1-4}$ aliphatic hydrocarbon groups substituted by a single carboxy, sulpho, acrylamido or an aryl group; Formula 17 gives a 3,2-HOPO-substituted analog of desferrioxamine-B. In Formulas 15–17, $R_1$ is also as given above for the monomers of Formula 9. The chelating agent of Formula 16 with a long hydrocarbon chain as the Z group is a promising extractant for actinides, especially Am(III).

The chelating agents of this invention also include amine compounds which, in addition to having at least one 3,2-HOPO structural unit, are also substituted with 1,2-HOPO analogs and catechol analogs. Thus, in the compounds of Formulas 10–16 above, the HOPO substituents could be replaced with the any of the structures given by Formulas 18 to 21, as long as one or more 3,2-HOPO substituents remain present on the chelating structure (where the free valency in each case indicates the preferred attachment point of the chelating group to a backbone).

Also included in the present invention are chelating agents having polymeric backbones and at least one amine functionality to which a HOPO substituent is bonded through an amide-type linkage. Examples of suitable polymers here include, but are not limited to, poly (styrenedivinylbenzene), agarose, and polyacrylamide.

The present invention also relates to novel methods of synthesizing the aforementioned chelating agents as outlined below.

The novel 3,2-HOPO compounds (represented below by the monomeric compound) shown in Formula 9–17 may be conveniently synthesized according to Scheme 1.

Scheme 1

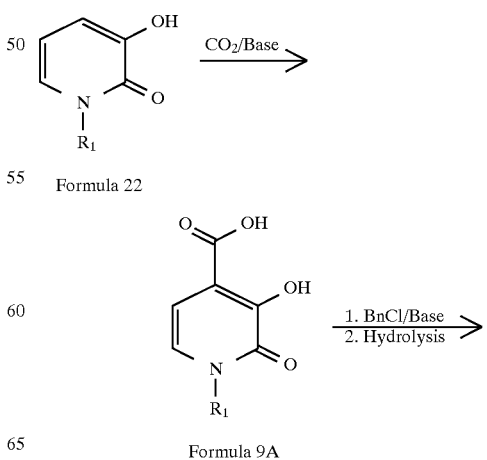

Formula 22

Formula 9A

-continued
Scheme 1

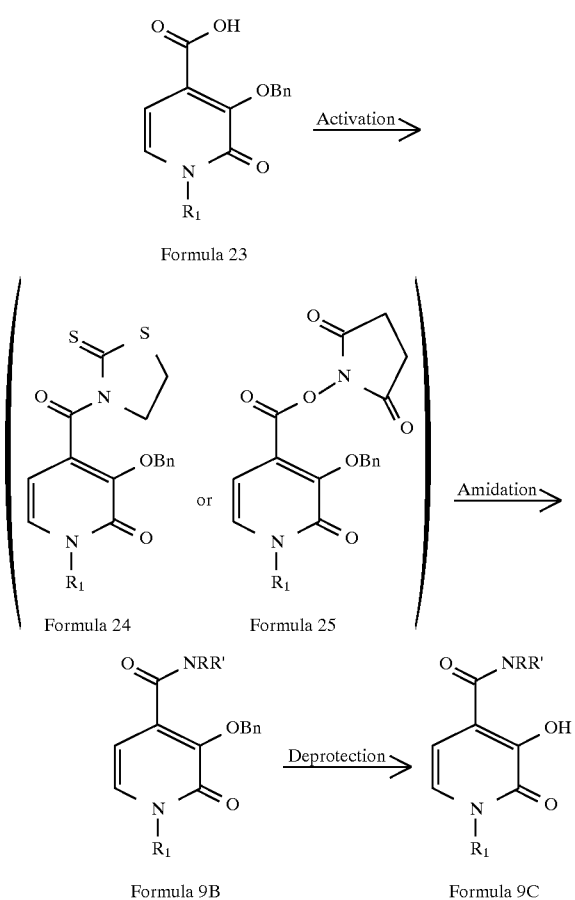

Wherein R=backbone, $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group, and R' is selected from the group consisting of: hydrogen, $C_{1-8}$ aliphatic hydrocarbon groups, and $C_{1-8}$ aliphatic hydrocarbon groups substituted by a single carboxy, sulpho, sulphamoyl, N-methyl or N-ethyl sulphamoyl group, or an aryl group.

The 4-carboxylic acid derivative (Formula 9A) of 1-alkyl-3-hydroxy-2-pyridinone is prepared from a 1-alkyl-3-hydroxy-2-pyridinone. The latter, for example, 1-methyl-3-hydroxy-2-pyridinone (Formula 22, $R_1$=methyl) is a known compound. However, the reported procedure is not safe and is neither convenient nor suitable for large scale production. The reported procedure is to put 3-hydroxy-2(1H)-pyridinone and iodomethane in a sealed glass tube and heat this mixture to 140° C. for two days. However, the size of the sealed glass tube is limited and yields only several grams of product. Furthermore, the pressure in the sealed glass tube may cause it to explode, thereby releasing toxic fumes. If the glass tube does not explode, the resultant material is treated with gaseous sulfur dioxide, a corrosive and toxic gas. In the final step, the compound is purified by recrystallization from petroleum ether, a method that is not safe, not convenient and is time consuming. Because Formula 9A is an important precursor to the present invention, the inventors have developed a safe and convenient procedure which can be used for large scale production as follows. 3-Hydroxy-2(1H)-pyridinone and iodomethane (1:1.05 mol ratio) are placed in a capped Teflon container, the container is put in a stainless steel Parr bomb and heated to 150° C. for 2 days. This container may be 50 times larger than the sealed glass tube and will not explode. The cooled bomb is opened and the resultant thick dark oil is mixed with sodium sulfite (1:1.5 mol ratio), which is not corrosive and toxic (as is gaseous sulfur dioxide) and dissolved in water. The solution is neutralized and then extracted with a suitable solvent. The 1-methyl-3-hydroxy-2-pyridinone may then be purified with a flash silica gel plug, which is much safer, convenient and time saving than recrystallization from hot petroleum ether. The reported procedure yields approximately 6 grams each batch. The present invention can yield approximately 300 grams by using a 1 liter capacity Parr bomb each time.

The 4-carboxylic acid shown in Formula 9A ($R_1$=alkyl) may then be prepared from the 3,2-HOPO compound of Formula 22 ($R_1$=alkyl) as follows. A quantity of the 3-hydroxy-2(1H)-pyridinone is mixed with anhydrous alkali metal carbonate, such as sodium or potassium carbonate, in a preferred mol ratio of 1:3 to 1:5. The dried mixture is then put in a Parr bomb and the bomb is then filled with dry carbon dioxide (850 psi) and heated to 170°–200° C. for 2 days. The cooled bomb is opened and the resultant solid is dissolved in water and treated with HCl, the 4-carboxylic acid may then be isolated as free acid form, e.g. by filtration recrystallization and dried (see Example 1).

The 3,2-HOPO ligands shown in Formulas 9C to 17 may be preferably prepared from the reaction of an amine backbone and the active protected intermediates. Thus the 1-alkyl-4-carboxy-3-hydroxy-2(1H)-pyridinone (Formula 9A) may conveniently be converted to the protected acid (Formula 23) through the protection of the 3-hydroxy group. Protection can be performed with an ether group, such as a benzyloxy group or a methoxy group. Benzyloxy protection is preferred because it can be easily deprotected by hydrogenation. Reaction of the protected acid with a compound to activate the acid (for example: 2-mercapto-thiazoline or N-hydroxysuccinimide (NHS)), in the presence of 1,3-dicyclohexylcarbodiimide (DCC) gives the activated intermediates (Formulas 24 or 25). This is reacted with the amine compound which will provide the "backbone" of the chelating agent at room temperature to give the protected 3,2-HOPO ligands generally as viscous oils. They are purified preferably by extraction and/or column chromatography. The hydroxy protecting groups may then be removed by hydrogenation and the final product may be recrystallized from methanol, ethyl acetate, or water.

The 3-benzyloxy-1-methyl-4-(2-thioxothiazolidin-1-yl) carbonyl-2(1H)-pyridinone (Formula 24) is a highly preferable intermediate: it is a bright yellow crystalline compound, easy to be prepared and purified. Unlike other activated intermediates such as 3-benzyloxy-1-methyl-4-(succinimidyloxy)carbonyl-2(1H)-pyridinone (Formula 25), it is stable and not sensitive to alcohol, water, or even dilute inorganic acid and base. It selectively reacts with primary amines to form amide products. The end of the reaction can be easily monitored by the disappearance of its characteristic yellow color.

While many amines can be used in this reaction to effect production of 3,2-HOPO-substituted chelating agents, preferred amines are those which correspond to the structures of Formulae 9–17. Particularly preferred amines are the polyamines: 1,5-diaminopentane $NH_2(CH_2)_5NH_2$), 2,2'-oxybis-(ethylamine), tris(2-aminoethyl)amine (see Formula 12, m=2), tris(aminomethyl)-benzene (see Formula 13), N,N,N',N'-tetra(2-aminoethyl)-ethylenediamine, also known as PENTEN (see Formula 14, m=n=2), and the monoamine desferrioxamine B (see Formula 17).

Other amines which may be used in the above synthetic procedure include compounds generally given by Formulas 10–13 but having one or more 1,2-HOPO, 3,2-HOPO and catechol moieties in addition to at least one 3,2-HOPO moiety. Organic polymers, both water-soluble and water-insoluble, having at least one amino group may also be used (e.g., agarose, polyacrylamide, polystyrene derivatives and other similar compounds).

The novel 3,2-HOPO compounds (represented below by the monomeric compound) shown in Formulas 9–17 are also conveniently synthesized according to Scheme 1-1.

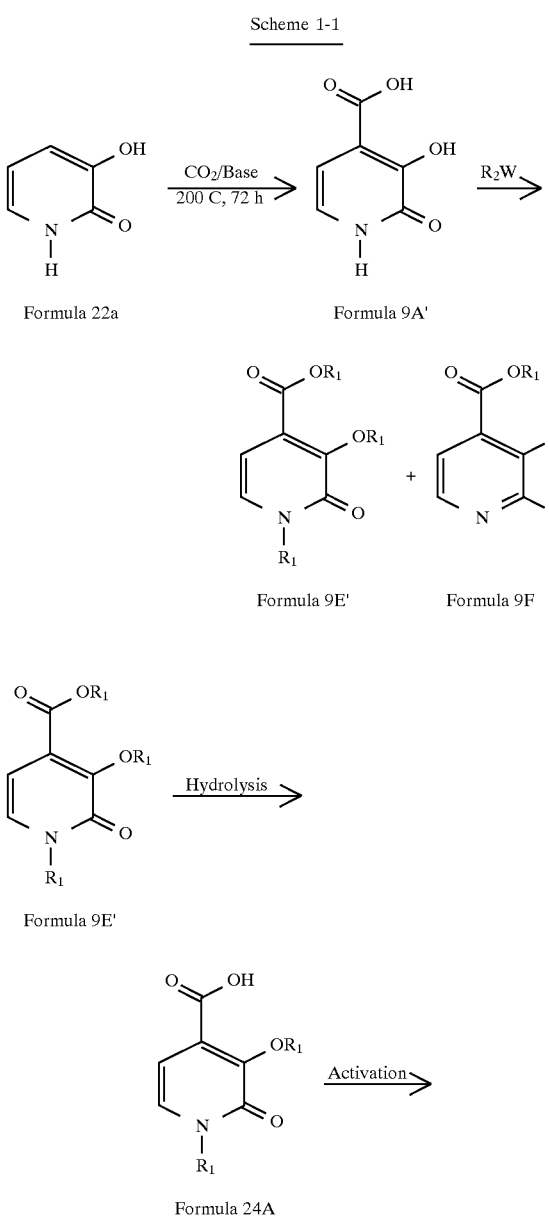

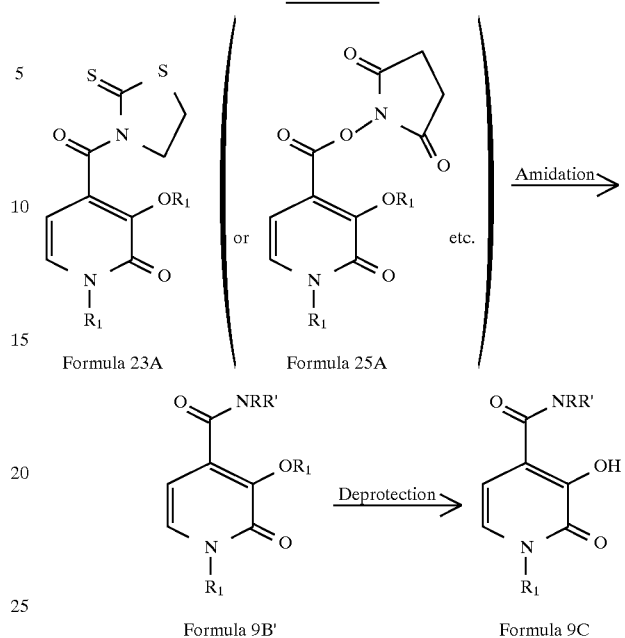

wherein R=backbone, $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group, and R' is selected from the group consisting of: hydrogen, $C_{1-8}$ aliphatic hydrocarbon groups, $C_{1-8}$ aliphatic hydrocarbon groups substituted by a single carboxy, sulpho, sulphamoyl, N-methyl or N-ethyl sulphamoyl group, or an aryl group, and W is generally chloride, bromide, or iodide.

Step 1: The 4-carboxylic acid shown in Formula 9A' is prepared from the commercially available 2,3-dihydroxypyridine (Formula 22A) as follows. A quantity of the 3-hydroxy-2(1H)-pyridinone is mixed with anhydrous potassium carbonate in a preferred mol ratio of 1:3 to 1:5. The dried mixture is then put in a Parr bomb and the bomb is then filled with dry carbon dioxide (850 psi) and heated to 200° C. for 2 days. The cooled bomb is opened and the resultant solid is dissolved in water and treated with HC1, the 4-carboxylic acid is then isolated in a free acid form, for example, by filtrating, recrystallizing and drying.

The 3,2-HOPO ligands shown in Formulas 9C to 17 are preferably prepared from the reaction of an amine backbone and the active protected intermediates. Thus the 4-carboxy-3-hydroxy-2(1H)-pyridinone (Formula 9A') is conveniently converted to the fully protected ester (Formula 9E and 9F) through the reaction with an alkylating agent, such as benzyl chloride or methyl iodide, in the presence of a base, such as potassium carbonate. Compounds 9E and 9F are easily separated by column chromatography.

Step 2: Compound 9E is converted into the protected acid (Formula 23A), and reaction of the protected acid with a compound to activate the acid (for example: 2-mercaptothiazoline or N-Hydroxysuccinimide (NHS)) in the presence of 1,3-dicyclohexyl-carbodiimide (DCC) gives the activated intermediates (Formulae 24A or 25A). This is reacted with the amine compound which will provide the "backbone" of the chelating agent at room temperature to give the protected 3,2-HOPO ligands generally as viscous oils. They are purified preferably by extraction and/or column chromatography. The hydroxy protecting groups are then removed by deprotection (for example using $BBr_3$ as a deprotecting agent) and the final product is recrystallized from methanol, ethyl acetate, or water.

Properties of the Novel Compounds

Physical Properties: The novel 3,2-HOPO compounds are white to pale-yellow in color. They are not hygroscopic in general and are obtained as micro-crystalline or amorphous solids. The monomers melt sharply, but the multidentate compounds decompose slowly upon heating. The most distinctive feature of their NMR spectra is the presence of two doublets in the aromatic region arising from the HOPO ring protons. The two doublets appear at d 6.4–6.6 and at d 6.6–7.2 ppm. The I.R. of the isolated compounds display a strong band at 1650–1680 $cm^{-1}$ due to the amide group. In addition to that band there are four strong bands in the region 1430–1600 $cm^{-1}$ due to the ring C=C and C—N stretching frequencies.

Chemical Properties: The 3,2-HOPO based amide compounds are in general slightly to moderately soluble in water, except the simple monomers, such as compound 1-methyl-4(1-propylcarbamoyl)-3-hydroxy-2(1H)-pyridinone (Formula 9C, R=1-propyl, R'=H), which is very soluble in water as well as organic solvents. They are nearly neutral (having $pK_a$'s on the order from 5 to 8), and the pH of saturated solutions typically are close to neutral. These compounds form stable complexes with various metal ions, such as $Fe^{3+}$, $Gd^{3+}$, $AM^{3+}$, $Pu^{4+}$, etc.

Experimental Methods

Infrared spectra were obtained with a Perkin-Elmer Model 283 spectrophotometer. The NMR spectra were obtained using UCB 250 (250 MHz), BVX 300 (300 MHz) and AM 500 (500 MHz) spectrometers. Mass spectral data were obtained with an Atlas MS11; a consolidated 12-110B, or a Kratos MS-50 spectrometer. The data can be tabulated as m/e. Elemental analyses were performed by the microanalytical Laboratory, Department of Chemistry, University of California, Berkeley.

Tris(3-aminopropyl)amine, 1,3,5-tris(aminomethyl)-benzene, N,N,N',N'-tetrakis(2-aminoethyl)ethylenediamine (PENTEN or H(2,2)-amine) can be prepared by methods described in the literature. N,N,N',N'-Tetrakis(2-aminoethyl)-1,3-propylenediamine (H(3,2)-amine), and N,N,N',N'-tetrakis(2-aminoethyl)-1,4-butylenediamine (H(4,2)amine) can be prepared in a manner similar to the preparation of PENTEN. Desferrioxamine B can be obtained from Ciba-Geigy. Other reagents and items disclosed can be purchased from Aldrich Chemical Co. and used as received.

Animal studies were completed using methods detailed in *Radiation Protection Dosimetry*, 1994, 53, 305: P. W. Durbin et al., "In Vivo Chelation of Am(III), Pu(IV), Np(V) and U(VI) in Mice by TREN-(Me-3,2-HOPO)"; *Radiation Protection Dosimetry*, 1989, 17, 351: P. W. Durbin et al., "Removal of $^{238}Pu(IV)$ from Mice by Polycatechoylate, -Hydroxamate or -Hydroxypyridinonate Ligands"; *Radiation Research*, 1984, 99, 85: P. W. Durbin et al., "Specific Sequestering Agents for the Actinides . . . "; *Radiation Research*, 1984, 99, 106: P. W. Durbin et al., "Removal of Pu and Am from Beagles and Mice . . . "; *Radiation Research*, 1980, 81, 170: R. D. Lloyd et al., and P. W. Durbin et al., "Specific Sequestering Agents for the Actinides . . . ". The foregoing articles are hereby incorporated by reference.

Radionuclides used in the animal studies came from a variety of sources. The $^{238}Pu(IV)$ citrate and $^{241}Am(III)$ citrate solutions were prepared for animal injection by 8- to 10-fold dilution with 0.14M NaCl (pH 4) of concentrated stock solutions (0.08M sodium citrate buffer) that had been held in frozen storage at Lawrence Berkeley Laboratory (hereinafter LBL) for several years. [The $^{238}Pu(IV)$ was originally obtained from D. R. Atherton at the University of Utah Radiobiology Laboratory, Salt Lake City. The $^{241}Am$ (III) solution had been obtained many years earlier from the LBL Actinide Chemistry group.]

The $^{237}Np(V)$ was obtained from J. Bucher of the LBL Actinide Chemistry group as $NpO_2Cl$ in 0.1M HCl. It was diluted to the desired radioactivity concentration in 0.14M NaCl and the pH was adjusted to about 4.5 with NaOH just before use.

The $^{232}U$ was obtained from the Isotope Products Laboratory, Burbank, Calif., and $^{234,235}U$ was obtained as U metal from long-held LBL storage. The two U sources were combined and dissolved in 6N $HNO_3$, dried, and redissolved in 0.1N HCl. The daughter radioactivities were removed by elution from a Dowex-50X4 column (22 cm length, 0.7 cm diameter, 1.5 mL $min^{-1}$ flow rate) with 3.2N HCl. The U fractions (previously identified by a trial run with $^{234,235}U$ alone) were combined, dried, and redissolved in 0.14M NaCl at pH 5.5.

All injection solutions, after dilution and pH adjustment, were sterilized by passing through a 0.22 $\mu m$ Millipore filter into 10 mL serum bottles fitted with rubber stoppers, and frozen until used.

Solutions were calibrated by alpha scintillation counting (Packard Tri-Carb 460C, Ecolume® scintillation fluid).

The current catalog of Isotope Products Laboratory, Burbank, Calif., lists for retail sale: $^{238}pU$, $^{241}Am$, $^{237}Np$, and $^{232}U$.

EXAMPLES

Example 1

Preparation of 3-benzyloxy-4-carboxy-1-methyl-2 (1H)-pyridinone and related precursors (1) 1-Methyl-3-hydroxy-2(1H)-pyridinone (Formula 22, $R_1$=methyl):

1-Methyl-3-hydroxy-2(1H)-pyridinone is a known material; however the previous procedure for preparation is neither safe nor suitable for large scale production. Therefore, the inventors have developed a safe and convenient procedure which can be used for large scale or industrial production after minor modification. The details are described as follows:

3-Hydroxy-2(1H)-pyridinone (34.44 g, 0.31 mol) and iodomethane (46.7 g, 0.33 mol) are placed in an 80 mL capped Teflon container (Caution: iodomethane is highly toxic), and put in a stainless steel Parr bomb and heated to 150°±10° C. for about 48–60 hours. The cooled bomb is opened and the resultant thick dark oil is mixed with sodium sulfite (64 g, 0.5 mol) and dissolved in 300 mL water to form a pale brown solution. The solution is neutralized to pH 7–8 and filtered to remove any insoluble impurity. The filtrate is then extracted with methylene chloride (4×100 mL). The combined extracts are dried, then applied to a flash silica gel plug (6 cm×8 cm) and eluted with 4% methanol in methylene chloride. The solvent is rotary evaporated to give the title compound (24.3 g, 62.6%) as colorless crystals, mp. 129°–130° C. $^1H$ NMR (250 MHz, $CDCl_3$): δ 3.621 (s, 3H), 6.144 (t, 1H, J=7.10), 6.79–6.85 (m, 2H), 7.27 (s,br, 1H).

Anal. for $C_6H_7NO_2$ (125.129), Calcd.(found): C, 57.59 (57.23); H, 5.64 (5.70); N, 11.20 (10.93).

(2) 4-Carboxy-1-methyl-3-hydroxy-2(1H)-pyridinone (Formula 9A, $R_1$=methyl)

1-Methyl-3-hydroxy-2(1H)-pyridinone (1) (6.25 g, 50 mmol) is mixed with anhydrous potassium carbonate (36 g, 0.26 mol). The vacuum dried mixture is put in a Parr bomb which is then filled with dry carbon dioxide gas (850 psi) and heated to 175°–185° C. for 3 days. The cooled bomb is opened and the resultant pale yellow solid is dissolved in ice water and acidified with 6N HCl to produce a beige crystalline product (7.42 g, 87.5%), m.p. 243°–245° C. (dec). $^1$H NMR (250 MHz, DMSO-$d_6$): δ 3.469 (s, 3H), 6.357 (d, 1H, J=7.33), 7.166 (d, 1H, J=7.19), 7.27 (s,br, 1H). $^1$H NMR (250 MHz, $D_2$O-NaOD): d 3.342 (s, 3H), 6.176 (d, 1H, J=6.94), 6.487 (d, 1H, J=7.00). Anal. for $C_7H_7NO_4$ (169.14): Calcd. found): C, 49.71 (49.74); H, 4.17 (4.30); N 8.28 (8.16).

3) 3-Benzyloxy-4-carboxy-1-methyl-2(1H)-pyridinone (Formula 23, $R_1$=methyl)

4-Carboxy-1-methyl-3-hydroxy-2(1H)-pyridinone (6.8 g, 0.04 mol) is mixed with benzyl chloride (12.1 g, 0.088 mol), anhydrous potassium carbonate (13.8 g, 0.1 mol) in anhydrous dimethylformamide (DMF) (120 mL). The mixture is heated at 75°–80° C. under $N_2$ in darkness for 16 hours. The reaction mixture is filtered and rotary evaporated to yield a dark oil, which is purified by a silica gel plug as mentioned in the synthesis of 1-methyl-3-hydroxy-2(1H)pyridinone above, to give the 3-benzyloxy-4-benzyloxycarbonyl-1-methyl-2(1H)-pyridinone as a pale yellow, thick oil. It is mixed with methanol (50 mL) and a 6M NaOH solution (10 mL). The mixture is stirred at room temperature for 4 hours, then evaporated to dryness. The residue is dissolved in water (100 mL), and acidified with 6M HCl solution to pH 2 to give the title compound (9.3 g 88.7%), as a white crystalline product, m.p. 152°–153° C. $^1$H NMR (250 MHz, $CDCl_3$): δ 3.616 (s, 3H), 5.611 (s, 2H), 6.695 (d, 1H, J=7.13), 7.152 (d, 1H, J=7.16), 7.35–7.48 (m, 5H). Anal. for $C_{14}H_{13}NO_4 \cdot 0.2 H_2O$ (262.87), Calcd. (found): C, 63.97 (64.05); H, 5.14 (5.14); N, 5.33 (5.18).

Example 2

Preparation of 3-benzyloxy-1-methyl-4-(2-thioxothiazolidin-1-yl)-carbonyl-2(1H)-pyridinone (Formula 24, $R_1$=methyl)

To a solution of 3-benzyloxy-4-carboxy-1-methyl-2(1H)-pyridinone (1.05 g, 4 mmol), 2-mercaptothiazoline (0.50 g, 4.2 mmol) and a catalytic amount of 4-dimethyl-aminopyridine (DMAP) in dry methylene chloride (50 mL), N, N'-dicyclohexyl-carbodiimide (DCC) (0.86 g, 4.2 mmol) is added. After stirring for 4 hours, the dicyclohexylurea (DCU) solids are removed by filtration, the yellow filtrate is rotary evaporated to give a yellow solid. Crystallization from isopropanol-methylene chloride gives the title compound (1.16 g, 80.4%) as bright yellow crystalline plates, m.p. 149°–150° C. $^1$H NMR (250 MHz, $CDCl_3$) δ 2.867 (t, 2H, J=7.32), 3.594 (s, 3H), 4.313 (t, 2H, J=7.33), 5.301 (s, 2H), 6.107 (d, 1H, J=6.99), 7.126 (d, 1H, J=7.00), 7.31–7.45 (m, 5H). Anal for $C_{17}H_{16}N_2O_3S_2$ Calcd. (found): C, 56.64 (56.36); H, 4.47 (4.47); N, 7.73 (7.73); S, 17.78 (17.41).

Example 3

Preparation of 3-hydroxy-1-methyl-4(1-propylcarbamoyl)-2(1H)-pyridinone (Formula 9C, $R_1$=methyl, R=n-propyl, R'=H)

(1) 3-Benzyloxy-1-methyl-4(1-propylcarbamoyl)-2(1H)-pyridinone (Formula 9B, $R_1$=methyl, R=n-propyl, R'=H)

To a solution of 3-benzyloxy-1-methyl-4-(2-thioxothiazolidin-1-yl)carbonyl-2(1H)-pyridinone (720 mg, 2 mmol) in dry methylene chloride (40 mL) is added n-propylamine (0.18 mL, 2.2 mmol) while stirring. The disappearance of the yellow color indicates the end of the amidation reaction. The reaction mixture is concentrated and loaded on a flash silica gel column. Elution with 2–6% methanol in methylene chloride allows the isolation of benzyl protected title compound (522 mg, 87%) as a colorless thick oil. $^1$H NMR (250 MHz, $CDCl_3$): δ 0.794 (t, 3H, J=7.40), 1.333 (q, 2H, J=7.23), 3.184 (q, 2H, J=7.0), 3.605 (s, 3H), 5.383 (s, 2H), 6.816 (d, 1H, J=7.24), 7.123 (d, 1H, J=7.21), 7.30–7.50 (m, 5H), 7.92 (s, br, 1H).

(2) 3-Hydroxy-1-methyl-4(1-propylcarbamoyl)-2(1H)-pyridinone (Formula 9C, $R_1$=methyl, R=n-propyl, R'=H)

3-Benzyloxy-1-methyl-4(1-propylcarbamoyl)-2(1H)-pyridinone (301 mg, 1 mmol) and 5% Pd/C catalyst (30 mg) are mixed with ethanol (15 mL), the mixture is stirred under hydrogen (1 atm) at room temperature for three hours. After filtration, the filtrate is rotary evaporated to give a pale pink solid. Crystallization from ethyl acetate gives the titled compound (180 mg, 86%) as a colorless crystalline product, m.p. 163.5°–165° C. $^1$H NMR (250 MHz, DMSO-$d_6$): δ 0.883 (t, 3H, J=7.41), 1.524 (q, 2H, J=7.30), 3.234 (q, 2H,J=6.57), 3.469 (s, 3H), 6.524 (d, 1H, J=7.43), 7.185 (d, 1H, J=7.42), 8.467 (s,br, 1H). MS (+FAB,TG/G): 211.1 (MH+, 100%). Anal. for $C_{10}H_{13}N_2O_3$ (209.228), Calcd. (found): C, 57.40 (57.44); H, 6.26 (6.63); N 13.39 (13.25).

Example 4

Preparation of 1,3-bis[(3-hydroxy-1-methyl-2-oxo-1,2-dihydropyridin-4-yl)carboxamido] propane (3-LI-Me-3,2- HOPO, Formula 10, $R_1$=methyl, a=3)

To a solution of 3-hydroxy-4-benzyloxycarbonyl-1-methyl-2(1H)-pyridinone (1.1 g, 4.2 mmol), 2-mercaptothiazoline (0.52 g, 4.4 mmol), and a catalytic amount of DMAP in dry methylene chloride (50 mL), DCC (0.90 g, 4.4 mmol) is added. The resulting yellow mixture is stirred in darkness for four hours, and 1,3-propanediamine (0.15 g, 2 mmol) is added neatly. The mixture is stirred overnight, and filtered to remove any DCU solids, the filtrate is rotary evaporated and loaded onto a flash silica column. Elution with 2–6% methanol in methylene chloride allows the separation of the benzyl-protected precursor (0.98 g) as a pale yellow thick oil. It is dissolved in glacial acetic acid (20 mL) and hydrogenated by using 10% Pd on charcoal as a catalyst. Filtration followed by rotary evaporation gives a pale brown residue which is recrystallized from methanol to give the title compound (555 mg, 73.3%) as a beige powder, m.p. 268°–271° C. (dec). $^1$H NMR (300 MHz, DMSO-$d_6$): δ 1.757 (t, 2H), 3.327 (q, 4H), 3.469 (s, 6H), 6.503 (d, 2H, J=7.24), 7.193 (d, 2H, J=7.28), 8.483 (s,br, 2H), 11.7 (s, br, 2H). MS (+FAB, NBA): 377.2 (MH+, 17%), 399.2 (MNa+, 11%). Anal. for $C_{17}H_{20}N_4O_6$ (376.375), Calcd. (found): C, 54.25 (54.17); H, 5.35 (5.49); N, 14.88 (14.59).

Example 5

Preparation of 1,4-bis[(3-hydroxy-1-methyl-2-oxo-1,2-dihydro-pyridin-4-yl)carboxamido]butane (4-LI-Me-3,2-HOPO, Formula 10, $R_1$=methyl, a=4)

This compound is prepared by the procedure of Example 4, except 1,4-butanediamine (160 mg, 1.8 mmol) is used instead of 1,3-propanediamine. Separation and purification of the benzyl-protected precursor are performed as described above, the pure precursor is recrystallized from methanol as a white crystalline solid, m.p. 189°–190° C. It is deprotected by catalytic hydrogenation as described above. The title compound is recrystallized from methanol to give a beige solid product (462 mg, 68.7%), m.p. 265° C. (dec). $^1$H NMR (300 MHz, DMSO-d$_6$): δ 1.541 (s, br, 2H), 3.308 (s, br, 4H), 3.463(s, 6H), 6.515 (d, 2H, J=7.31), 7.187 (d, 2H, J=7.27), 8.483 (t, br, 2H J=5.34). MS (+FAB, NBA): 391.3 (MH$^+$, 100%), 413.1 (MNa$^+$, 25%). Anal. for C$_{18}$H$_{22}$N$_4$O$_6$. 0.5 H$_2$O (399.41), Calcd. (found): C, 54.13 (54.67); H, 5.80 (5.91); N, 14.02 (13.58).

Example 6

Preparation of 1,5-bis[(3-hydroxy-1-methyl-2-oxo-1,2-dihydro-pyridin-4-yl)carboxamido]pentane (5-LI-Me-3,2-HOPO, Formula 10, R$_1$=methyl, a=5)

This compound is prepared by the procedure of example 4, except 1,5pentane-diamine (0.21 g, 2mmol) is used instead of 1,3-propanediamine. Separation and purification of the benzyl-protected precursor are performed as described above, the pure precursor is separated as a pale yellow oil. It is deprotected by catalytic hydrogenation as described above. The deprotected product is recrystallized from methanol to give the title compound (530 mg, 65.7%) as white scale-like micro crystalline product. m.p. 225°–6° C. (dec). $^1$H NMR (300 MHz, DMSO-d$_6$): δ 1.32 (m, 2H), 1.527 (qin, 4H, J=7.17), 3.276 (q, 4H, J=6.49), 3.464 (s, 6H), 6.509 (d, 2H, J=7.33), 7.183 (d, 2H, J=7.34), 8.459 (t, br, 2H, J=5.52). MS (+FAB, NBA): 405 (MH$^+$, 100%), 427.1 (MNa$^+$, 25%). Anal. for C$_{19}$H$_{24}$N$_4$O$_6$. 0.56H$_2$O (415.24), Calcd. (found): C, 54.96 (54.89); H, 6.12 (5.99); N, 13.45 (13.27).

Example 7

Preparation of 1,6-bis[(3-hydroxy-1-methyl-2-oxo-1,2-dihydropyridin-4-yl)carboxamido]hexane (6-LI-Me-3,2-HOPO, Formula 10, R$_1$=methyl, a=6)

This compound is prepared by the procedure of example 4, except 1,6-hexane-diamine (220 mg, 1.9 mmol) is used instead of 1,3-propanediamine. Separation and purification of the benzyl-protected precursor are performed as described above, the pure precursor is recrystallized from methanol as a white crystalline solid, m.p. 179°–180° C. It is deprotected by catalytic hydrogenation as described above. The title compound is recrystallized from methanol to give a white solid product (530 mg, 73.3%), m.p. 240°–1° C. (dec). $^1$H NMR (300 MHz, DMSO-d$_6$): δ 1.32 (s, br, 4H), 1.501 (t, br, 4H, J=6.62), 3.258 (q, 4H, J=6.55), 3.452 (s, 6H), 6.502 (d, 2H, J=7.22), 7.183 (d, 2H, J=7.34), 8.455 (t, br, 2H, J=5.36), 11.8 (s, br). MS (+FAB, NBA): 419.2 (MH$^+$, 10%), 441.2 (MNa$^+$, 29%), 463.2 (M+Na$^+$–H$^+$, 15%). Anal. for C$_{20}$H$_{26}$N$_4$O$_6$. 0.25 H$_2$O (422.96), Calcd. (found): C, 56.79 (57.03); H, 6.31 (6.41)); N, 13.24 (12.95).

Example 8

Preparation of 1,5-bis[(3-hydroxy-1-methyl-2-oxo-1,2-dihydro-pyridin-4-yl)carboxamido]-3-oxypentane (5-LI-O-Me-3,2-HOPO, Formula 11, Z=O, a=b=2)

This compound is prepared by the procedure of Example 4, except that 2,2'-oxybis(ethylamine) (0.15 g, 1.4 mmol) is used instead of 1,3-propanediamine. Separation and purification of the benzyl-protected precursor are performed as described above, the pure precursor is separated as a pale yellow oil. It is deprotected by catalytic hydrogenation as described above. The title compound is recrystallized from methanol to give a white solid product (510 mg, 89%), m.p. 205° C. (dec). $^1$H NMR (300 MHz, DMSO-d$_6$): δ 3.327 (t, 4H), 3.404. (s, 6H), 3.488(t, 4H, J=5.32), 6.452 (d, 2H, J=7.33), 7.107 (d, 2H, J=7.31), 8.483 (s, br, 2H). MS (+FAB, NBA): 407.2 (MH$^+$, 100%), 429.2 (MNa$^+$, 72%). Anal. for C$_{18}$H$_{22}$N$_4$O7 (408.20), Calcd. (found): C, 53.19 (53.01); H, 5.48 (5.50); N, 13.72 (13.62).

Example 9

Preparation of N,N,N,-tris[(3-benzyloxy-1-methyl-2-oxo-1,2-dihydropyridin-4-yl)carboxamidoethyl]-amine (TREN-Me-3,2-HOPO, Formula 12, c=1)

To a solution of 3-benzyloxy-1-methyl-4-2-thioxothiazolidin-1-yl)carbonyl-2(1H)-pyridinone (Formula 24, 1.44 g, 4 mmol) in methylene chloride (50 mL), freshly distilled tris(2-aminoethyl)amine (TREN) (0.18 g, 1.2 mmol) is added, the mixture is stirred overnight and then rotary evaporated and loaded onto a flash silica column. Elution with 2–7% methanol in methylene chloride allows for isolation of the pure benzyl-protected precursor as a pale yellow oil. It is dissolved in glacial acetic acid (10 mL) and hydrogenated by using 10% Pd on charcoal as catalyst. Filtration followed by rotary evaporation gives a pale brown residue which is recrystallized from water to give the title compound (486 mg, 67.1%) as a pale yellow crystalline solid, m.p. 130°–2° C. (dec). $^1$H NMR (250 MHz, DMSO-d$_6$): δ 2.296 (t, 6H, J=5.97), 3.072 (q, 6H, J=5.82), 3.449 (s, 9H, NCH$_3$), 6.458 (d, 3H, J=7.24), 7.122 (d, 3H, J=7.27), 8.46 (t, br, 3H, J=5.3). $^1$H NMR (250 MHz, D$_2$O-N$_a$OD): δ 2.901 (t, 6H, J=6.26), 3.450 (s, 9H), 3.520 (t, 6H, J=6.24), 6.568 (d, 3H, J=7.29), 6.609 (d, 3H, J=7.21). MS (+FAB, NBA): 600.3 (MH$^+$). Anal. for C$_{27}$H$_{33}$N$_7$O$_9$. 1.5 H$_2$O (626.634) Calcd.(found): C, 51.75 (51.84)); H 5.79 (5.54); N 15.64 (15.59).

Example 10

Preparation of N,N,N,-tris[(3-benzyloxy-1-methyl-2-oxo-1,2-dihydro-pyridin-4-yl)carboxamidopropyl] amine (TRPN-Me-3,2-HOPO, Formula 12, c=2)

This compound is prepared by the procedure of TREN-Me-3,2-HOPO, except tris(3-aminopropyl)amine (TRPN) (0.16 g, 1.1 mmol) is used instead of TREN. Separation and purification of the benzyl-protected precursor are performed as described in example 9. The title compound (392 mg, 56.6%) is obtained by catalytic hydrogenation deprotection followed by precipitation from methanol/ether mixture and collected by filtration as a pale, greenish-yellow solid, m.p. 165° C. (dec) $^1$H NMR (250 MHz, DMSO-d$_6$): δ 1,710 (s, br 6H), 2.660 (s, br, 6H), 3.302 (s, br, 6H), 3.429 (s, 9H), 6.485 (d, 3H, J=7.30), 7.065 (d, 3H, J=7.30), 8.80 (s, br, 3H). $^1$H NMR (250 MHz, D$_2$O-NaOD): δ 1,756 (s, br 6H), 2.592 (s, br, 6H), 3.330 (s, br, 6H), 3.374 (s, 9H), 6.516 (d, 3H, J=7.27), 6.617 (d, 3H, J=7.17). MS (+FAB, TG/G): 642.2 (MH+, 85%). Anal. for C$_{30}$H$_{39}$N$_7$O$_9$. H$_2$O (659.707), Calcd. (found): C, 54.62 (54.40); H, 6.26 (6.27); N, 14.86 (14.82).

Example 11

Preparation of N,N,N,-tris[(3-hydroxy-1-methyl-2-oxo-1,2-dihydropyridin-4-yl)carboxamidoethyl]-aniline (ME-Me-3,2-HOPO, Formula 13)

To a solution of 3-benzyloxy-1-methyl-4-(2-thioxothiazolidin-1-yl)carbonyl-2(1H)-pyridinone (Formula 24, 400 mg, 1.1 mmol) in methanol (10 mL), a solution of mesitylenetriamine trihydrochloride (82 mg, 0.3 mmol) in pyridine/water (4:1, 10 mL) is added, the mixture is stirred overnight and rotary evaporated to dryness. The residue is dissolved in methylene chloride and loaded onto a flash silica column. Elution with 2–8% methanol in methylene chloride allows for isolation of the pure benzyl-protected precursor as a pale yellow oil, which solidifies upon standing. The title compound (118 mg, 58.3%) is obtained by catalytic hydrogenation deprotection of the precursor followed by recrystallization from methanol as a white solid, m.p. 168°–70° C. (dec). $^1$H NMR (300 MHz, DMSO-$d_6$): δ 3.470 (s, 9H), 4.463 (d, 6H, J=5.54), 6.495 (d, 3H, J=7.26), 7.147 (s, 3H), 7.159 (d,3H,J=7.64), 8.913(t, 3H,J=5.75). MS(+FAB,NBA): 619.2 (MH$^+$,100%), 641.2 (MNa$^+$, 20%). Anal. for $C_{30}H_{30}N_6O_9$. 1.9 $H_2O$ (652.84), Calcd.(found): C, 55.19 (55.31); H, 5.19 (5.19); N, 12.87 (12.62).

Example 12

Preparation of N,N,N',N'-tetrakis[(3-hydroxy-1-methyl-2-oxo-1,2-dihydropyridin-4-yl)carboxamido-ethyl]-ethylenediamine (H(2,2)-Me-3,2-HOPO, Formula 14, d=e=2)

To a solution of 3-benzyloxy-1-methyl-4-(2-thioxothiazolidin-1-yl)carbonyl-2(1H)-pyridinone (Formula 24, 1.44 g, 4 mmol) in methylene chloride (50 mL), N,N,N',N'-tetrakis(2-aminoethyl)ethylenediamine (PENTEN) (258 mg, 0.9 mmol) is added. After stirring for four hours, the mixture is filtered and evaporated to dryness. The residue is loaded onto a flash silica column. Elution with 3–8% methanol in methylene chloride allows for isolation of the pure benzyl-protected precursor as a pale yellow oil. It is dissolved in glacial acetic acid (20 mL), 20% Pd(OH)$_2$ on charcoal catalyst is added and the mixture is hydrogenated under 400 psi at room temperature overnight. Filtration followed by rotary evaporation gives a pale brown residue which is recrystallized from methanol to give the title compound (397 mg, 52.9%) as a white powder, m.p. 270° C. (dec). $^1$H NMR (250 MHz, DMSO-$d_6$): δ 2.663 (s,br, 12H), 3.35 (m,br, 8H), 3.436 (s, 12H), 6.465 (d, 4H, J=7.26), 7.093 (d, 4H, J=7.35H), 8.5 (s, br, 4H). MS (+FAB, NBA): 837.3 (MH$^+$, 100%). Anal. for $C_{38}H_{48}N_{10}O_{12}$. $H_2O$ (854.884), Calcd.(found): C, 53.39 (53.29); H, 5.89 (5.71); N 16.38 (16.10).

Example 13

Preparation of N,N,N',N'-tetrakis[(3-hydroxy-1-methyl-2-oxo-1,2-dihydropyridin-4-yl)carboxamido-ethyl]-propylenediamine (H(3,2)-N-Me-3,2-HOPO, Formula 14, m=3, n=2)

This compound is prepared by the procedure of H(2,2)-Me-3,2-HOPO, except N,N,N',N'-tetrakis(2-minoethyl]propylenediamine (H(3,2)-amine) (76 mg, 0.25 mmol) is used instead of PENTEN. Separation and purification of the benzyl-protected precursor are performed as described in example 12. The title compound (110 mg, 51.5%) is obtained by catalytic hydrogenation deprotection of the precursor followed by recrystallization from methanol as a greenish pale yellow solid, m.p. 141° C. (dec). $^1$H NMR (300 MHz, DMSO-$d_6$): δ 1.639 (s,br, 2H), 2.644 (s,br, 4H), 2.724 (s, br, 8H), 3.400 (s, br, 8H), 3.424 (s, 12H), 6.448 (d, 4H, J=7.19), 7.040 (d, 4H, J=7.23), 8.778 (s,br, 4H). MS(+FAB, NBA): 851.3 (MH+, 45%). Anal. for $C_{39}H_{50}N_{10}O_{12}$. 1.2$H_2O$ (875.52), Calcd.(found): C, 53.69 (53.70); H, 6.05 (5.98); N, 16.05 (16.09).

Example 14

Preparation of N,N,N',N'-tetrakis[(3-hydroxy-1-methyl-2-oxo-1,2-dihydropyridin-4-yl) carboxamido-ethyl]-butylenediamine (H(4,2)-Me-3, 2-HOPO, Formula 14, d=4, e=2)

This compound is prepared by the procedure of H(2,2)-Me-3,2-HOPO, except N,N,N',N'-tetrakis(2-aminoethyl)-butylenediamine (H(4,2)-amine) (80 mg, 0.25 mmol) is used instead of PENTEN. Separation and purification of the benzyl-protected precursor are performed as described in example 12. The title compound (125 mg, 58.3%) is obtained by catalytic hydrogenation deprotection followed by recrystalli-zation from methanol as a pale yellow solid, m.p. 124° C. (dec). $^1$H NMR (300 MHz, DMSO-$d_6$): δ 1.656 (s, br, 2H), 2.719 (s, br, 4H), 2.844 (s,br, 8H), 3.411 (s, br, 8H), 3.450 (s, 12H), 6.403 (d, 4H, J=7.19), 6.969 (d, 4H, J=7.32), 8.811 (s, br, 4H). MS (+FAB, NBA): 865.4 (MH$^+$, 66%). Anal. for $C_{40}H_{52}N_{10}O_{12}$. 2.2$H_2O$ (904.56), Calcd. (found): C, 53.06 (53.11); H, 6.28 (6.28); N, 15.47 (15.48).

Example 15

Preparation of DFO-1-Me-3,2-HOPO (Formula 17)
(1) Fe(II)-Bn-DFO-1-Me-3,2-HOPO-Complex The mesylate salt of DFO (Desfera, 2.63 g, 4 mmol) and $FeCl_3$.6 $H_2O$ (1.08 g, 4 mmol) are dissolved in methanol (120 mL) in a 250 mL round flask. To this purple-red solution, KOH solution (1.018N KOH in methanol (Aldrich), 11.7 mL) is added slowly, while stirring. To the above red Fe(III)-DFO complex (free amine species) solution, a solution of 3-benzyloxy-1-methyl-4-(2-thioxothiazolidinyl)carbonyl-2-(1H)-pyridinone (Formula 24, 1.44 g, 4 mmol) in methanol (50 mL) is added slowly, while stirring and the mixture is then stirred overnight. TLC on silica reveals the formation of benzyl protected Fe(III)-1-Me-3,2-HOPO-DFO complex. The red mixture is evaporated to dryness, then loaded on a flash silica column and gradient eluted with 4–20% methanol in methylene chloride. The main red fraction which shows only one spot on TLC (silica) plate is collected and evaporated to dryness, yielding 2.73 g (3.08 mmol, 77.2% based on DFO) of Fe(III)-Bn-DFO-1-Me-3,2-HOPO Complex. Anal. for $C_{39}H_{56}N_{70}$11Fe. 2$H_2O$ (890.805), Calcd. (found): C, 52.58 (52.99); H, 6.79 (7.25); N, 11.00 (11.19); Fe, 6.26 (5.97).
(2) Bn-DFO-1-Me-3,2-HOPO The above Fe(III)-Bn-DFO-1-Me-3,2-HOPO Complex (2.56 g, 3.0 mmol) is dissolved in a minimum amount of water and the pH is adjusted to above 13 with a 12M NaOH solution. The turbid solution is then filtered to remove the brown Fe(OH)$_3$ precipitate. The slight yellow filtrate is acidified with 6M HCl, at which point the protected DFO-Me-3,2-HOPO separates as very thick pale yellow oily material. After cooling, the oily product is solidified, it is triturated with the mother liquor and then filtered. The title compound (1.24 g, 51.7%) is obtained after washing with cold water, methanol and drying as a white solid product, m.p. 110°–2° C. $^1$H NMR (300 MHz, DMSO-$d_6$): δ 1.2–1.5 (m, 18H), 1.967 (s, 3H), 2.276 (t, J=7.04, 4H), 2.586 (t, J=6.83, 4H), 3.007 (q, J=6.14, 2H), 3.456 (t, J=6.94, 6H), 5.203 (s, 2H), 6.262 (d, 1H, J=7.02), 7.3–7.5 (m, 5H), 7.528 (d, 1H, J=7.03), 7.807 (t, br, 2H, J=5.04), 8.220 (t, br, J=5.41), 9.6 (s, br, 3H). MS (+FAB, NBA): m/e 802.4 (MH$^+$, 100%). Anal. for $C_{39}H_{59}N_7O_{11}$. $H_2O$ (819.966), Calcd. (found): C, 57.13 (57.37); H, 7.50 (7.64); N, 11.96 (11.78).
(3) DFO-Me-3,2-HOPO (Formula 17)

Bn-DFO-Me-3,2-HOPO (0.82 g, 1 mmol) is suspended in methylene chloride (20 mL) in a Schienk flask with a teflon stopcock. Under a flow of argon, the suspension is cooled to 0° C. before boron tribromide (1.9 mL, 20 mmol) is injected. The yellow slurry is stirred at room temperature for 72 hours before pumping off the excess $BBr_3$ and $CH_2Cl_2$. The remaining pale yellow solid is suspended in cold water. The raw product is collected by filtration, and then dissolved in a 1M NaOH solution. The solution is then acidified to pH 3 and the resultant precipitate is filtered off and dried to give the title compound (0.37 g, 53%) as a white solid, m.p. 166°–8° C. (dec). $^1$H NMR (300 MHz, DMSO-$d_6$) δ 1.20–1.52 (m, 18H), 1.962 (s, 3H), 2.261 (t, 4H, J=7.18), 2.571 (t, 4H, J=7.14), 2.993 (q, 4H, J=6.32), 3.251 (q, 2H, J=6.48), 3.450 (t, 6H, J=7.34), 3.458 (s, 3H), 6.514 (d, 1H, J=7.24), 7.182 (d, 1H, J=7.30), 7.778 (t, br, 2H, J=5.17), 8.484 (t, br, 1H, J=5.02), 9.617 (s, 2H), 9.660 (s, 1H). MS (+FAB, NBA): 712.4 (MH$^+$, 85%), 734.4 (MNa$^+$, 82%), 696.4 (60%). Anal. for $C_{32}H_{53}N_7O_{11}$ (711.824), Calcd. (found): 53.99 (54.19), 7.50 (7.53), 13.77 (13.48).

Example 16

Preparation of TREN-bis-Me-3,2-HOPO-bis-acetic acid (Formula 15)

(1) N,N-Bis[(3-benzyloxy-1-methyl-2-oxo-1,2-dihydropyridin-4-yl)-carboxamido-ethyl-N-(2-aminoethyl) amine (Bn-TREN-Bis-Me-3,2-HOPO, Formula 16, Z=$CH_2CH_2NH_2$)

To a solution of 3-benzyloxy-1-methyl-4-(2-thioxo-thiazolidin-1-yl)carbonyl-2(1H)-pyridinone (Formula 24, 3.2 g, 8.8 mmol) in $CH_2Cl_2$ (150 mL), a solution of TREN (0.63 g, 4.4 mmol) in 150 mL $CH_2Cl_2$ is added drop by drop over 16 hours. The reaction mixture is concentrated, loaded on a flash silica gel column (φ 40×80 mm), and eluted with 4% methanol in methylene chloride to separate 2-mercaptothiazoline and other byproducts. The title compound remains on the top of the column and is separated by further gradient elution with 4–6% $CH_3OH$+0.4% Triethylamine. The appropriate fractions are collected and evaporated to give 1.98 g (71%) of a white solid. This is a very useful intermediate to synthesize various mixed 3,2-HOPO chelating agents. $^1$H NMR (300 MHz, $CDCl_3$): δ 2.347 (m, 6H), 2.484(m, 2H), 3.198 (q, 4H, J=5.97), 3.591 (s, 6H), 5.324 (s, 4H), 6.714 (d, 4H, J=7.20), 7.117 (d, 4H, J=7.20), 7.27–7.43 (m, 10H), 7.978 (s br, 2H).

(2) Ethylenediamine-N,N-bis[(3-hydroxy-1-methyl-2-oxo-1,2-dihydropyridin-4-yl carboxamidoethyl]-N',N'-diacetic acid) (TREN-bis-Me-3,2-HOPO-bis-acetate, Formula 15)

N,N-Bis[(3-benzyloxy-1-methyl-2-oxo-1,2-dihydropyridin-4-yl)carboxamidoethyl-N-(2-aminoethyl)amine (2.0 g, 3.2 mmol), benzyl 2-bromoacetate (2.29 g, 10 mmol) and anhydrous $K_2CO_3$ (1.5 g, 10 mmol) are combined in dry THF (50 mL). The stirred mixture is warmed to 60° C. overnight under nitrogen. After cooling to room temperature, the reaction mixture is filtered, the filtrate is rotary evaporated and applied to a flash silica gel column. Elution with 0.5–4.0% $CH_3OH$ in $CH_2Cl_2$ produces a pale yellow thick oil as pure benzyl protected precursor. It is dissolved in glacial acetic acid (20 mL), 20% Pd(OH)$_2$ on charcoal catalyst (200 mg) is added and the mixture hydrogenated under 400 psi at room temperature overnight. Filtration followed by rotary evaporation gives a pale brown residue which is recrystallized from methanol to give the title compound (0.93 g, 53.1%) as a white powder, m.p. 194°–6° C. (dec). $^1$H NMR (500 MHz, $D_2O$): δ 3.291 (s, br, 4H), 3.367 (s, 6H), 3.38–3.39 (m, br, 2H), 3.40–3.42 (m, br, 2H), 3.542 (s, br, 3.791 (s, NH), 6.351 (d, 2H, J=4.35), 6.839 (d, 2H, J=4.34). MS (+FAB, TG/G): 565.2(MH$^+$, 100%), 587.2 (MNa$^+$, 20%). Anal for $C_{24}H_{32}N_6O_{10}$. 1.2 $H_2O$ (582.824), Calcd. (found): C, 49.17 (49.68); H, 5.91 (6.15); N, 14.33 (13.98).

Example 17

Preparation of Thorium (IV) Complex with 4-(1-propylcarbamoyl)-(1H)-pyridinone

To a solution of 1-Me-3,2-HOPO propylamide (Formula 9B, R=methyl, R'=H, 84 mg, 0.40 mmol) in dry acetonitrile (10 mL), a solution of thorium acetylacetonate (63 mg, 0.1 mmol) in acetonitrile (10 mL) is added while stirring. The clear mixture solution turns turbid after a few minutes, it is refluxed overnight under nitrogen. The resultant precipitate is filtered off and dried to give the title compound (66 mg, 88%) as a beige solid, m.p. 216°–8° C. $^1$H NMR (300 MHz, DMSO): δ 0.666 (t, 12H, J=7.39), 1.158 (q, 8H, J=7.17), 2.956 (q, 8H, J=6.47), 3.487 (s, 6H), 6.819 (d, 2H, J=7.03), 6.974 (d, 2H, J=7.19), 9.397 (t, 4H, J=5.57). MS (+FAB, TG/G) 1069.7 (ThL$_4$H$^+$, 50%), 859.3 (ThL$_3$+, 100%). Anal. for $ThC_{40}H_{52}N_8O_{12}$. 2.5$H_2O$ (1114.43), Calcd. (found): C, 43.11 (43.13); H, 5.15 (4.91); N, 10.05 (9.79).

Example 18

Preparation of Ferric Ion Complex with 1,3-Bis[(3-hydroxy-1-methyl-2-oxo-1,2-dihydropyridin-4-yl) carboxamido]propane To a suspension of 3-LI-Me-3,2-HOPO (Formula 10, m=3, 245 mg, 0.65 mmol) in dry methanol (10 mL), 0.65 mL of 1.018M KOH/methanol (Aldrich) is added to make a clear solution. A solution of ferric acetylacetonate complex (140 mg, 0.4 mmol) in dry methanol (10 mL) is added to the above ligand solution while stirring and results in a deep red color. The solution is evaporated under vacuum to give a black-red powdery solid, which is loaded on a lipophilic Sephadex (LH 20) column and eluted with methanol. The deep red band is collected and rotary evaporated to give the title complex (160 mg, 65%) as a powdery red-black solid. MS (+FAB, NBA): 1235.7 (MH$^+$,100%), shows typical isotope distribution for iron compounds. Anal. for $Fe_2C_{51}H_{54}N_{12}O_{18}$. $H_2O$ (1252.79), Calcd. (found): C, 48.89 (48.66); H, 4.50 (4.71); N, 13.41 (13.23); Fe, 8.91 (8.75).

Example 19

Preparation and Crystal Structure of Ferric Ion Complex with N,N,N,Tris[(3-hydroxy-1-methyl-2-oxo-1,2-dihydropyridin-4-yl)-carboxamidoethyl]-amine (Fe(III)-TREN-3,2-HOPO complex)

To a solution of TREN-Me-3,2-HOPO (63 mg, 0.10 mmol) in distilled water (20 mL), a solution of $FeCl_3$ (27 mg, 0.1 mmol) in water (5 mL) is added while stirring. The purple-red mixture solution is neutralized with saturated $NaHCO_3$ solution. The complex deposits upon standing overnight. It is filtered out and dried to give the title complex (62 mg, 95%) as black-red crystals. MS (+FAB, NBA): 653.3 (MH$^+$, 61%), shows an isotopic distribution typical for iron complexes. Anal. for $FeC_{27}H_{30}N_7O_9$. $H_2O$ (670.45), Calcd. (found): C, 48.37 (48.36); H, 4.81 (5.01); N, 14.62 (14.38).

Crystals of this compound suitable for x-ray diffraction are prepared by vapor diffusion of ether into its wet DMF solution. Its chemical formula is $2FeC_{29}H_{30}N_7O_9$. 2$H_2O$. $C_3H_7NO$. Its crystal structure is shown in FIG. 1 and the crystallographic data and parameters for this compound are shown in Table 1. The structure reveals extensive π-electron delocalization and a strong hydrogen bonding between the amide proton and its adjacent HOPO oxygen donor, as shown in Formula 8.

TABLE 1

Crystallographic Data and Parameters for
$2FeC_{29}H_{30}N_7O_9 \cdot 2H_2O \cdot C_3H_7NO$

| Formula: | $2FeC_{29}H_{30}N_7O_9 \cdot 2H_2O \cdot C_3H_7NO$ |
|---|---|
| Formula Weight (amu) | 1487.13 |
| Temperature (°C.) | −116 |
| Crystal System | triclinic |
| Space Group (#) | P1 (#2) |
| Cell Constants[a] | |
| a (Å) | 12.774(3) |
| b (Å) | 12.838(4) |
| c (Å) | 20.740(7) |
| α (°) | 91.33(3) |
| β (°) | 92.92(2) |
| γ (°) | 102.72(3) |
| Z | 4 |
| V (Å³) | 3311(3) |
| Abs. Coeff., $\mu_{calc}$ (cm⁻¹) | 5.46 |
| $d_{calc}$ | 1.49 |
| F (000) | 1540 |
| Crystal dimensions (mm) | 0.65 × 0.50 × 0.20 mm |
| Radiation | Mo—Ka (1 = 0.71073) |
| Diffractometer | Enraf-Nonius CAD-4 |
| h, k, l range collected | 0→13, −13→+13, −22→+22 |
| 2θ range | 3°–45° |
| Scan Type | Omega-2Theta |
| Scan speed (θ, °/min.) | 5.49°/min |
| Reflections collected | 8625 |
| Unique reflections: | 8625 |
| Reflections with ($F_o^2 > 3*\sigma(F_o^2)$) | 6168 |
| Number of parameters | 901 |
| Data/parameter ratio | 6.8 |
| R = [Σ\|ΔF\|/Σ\|Fo\|] | 0.081 |
| $R_w = [\Sigma w(\Delta F)^2/\Sigma w F_o^2]$ | 0.103 |
| GOF | 2.994 |
| Final Diff. $\rho_{max}$ (e⁻/Å³) | +1.3[b] |

[a] unit cell parameters and their esd's were derived by a least-squares fitting of the setting angles of 24 reflections in the range 9.9 ≤ 2θ ≤ 13.9°.
[b] Located near Fe 2.

Example 20

Preparation and Crystal Structure of Gadolinium (III) Ion Complex with N,N,N,-Tris[(3-hydroxy-1-methyl-2-oxo-1,2-dihydropyridin-4-yl) carboxamidoethyl]-amine (Gd(III)-TREN-3,2-HOPO complex)

To a solution of TREN-Me-3,2-HOPO (63 mg, 0.10 mmol) in dry methanol (10 mL), a solution of gadolinium nitrate pentahydrate (43 mg, 0.1 mmol) in dry methanol (10 mL) is added while stirring. The clear solution turns turbid after 2 drops of dry pyridine are added. The mixture is refluxed overnight under nitrogen, during which time the complex deposits as a white fluffy precipitate. It is filtered out, rinsed with cold methanol, and dried to give the title complex (66 mg, 88%) as a white solid. MS (+FAB, NBA): 753.3 (MH+, 100%), shows an isotopic distribution typical for gadolinium compounds. Anal. for $GdC_{27}H_{30}N_7O_9 \cdot 1.4H_2O$ (779.05), Calcd. (found): C, 41.62 (41.70); H, 4.24 (4.26); N, 12.58 (12.28).

This complex is very stable in aqueous solution with a formation constant log $\beta_{110}$ of 20.3 and a pM value for $Gd^{3+}$ of 19. This is substantially more stable than any of the $Gd^{3+}$ MRI agents in current clinical use.

Figure 2:
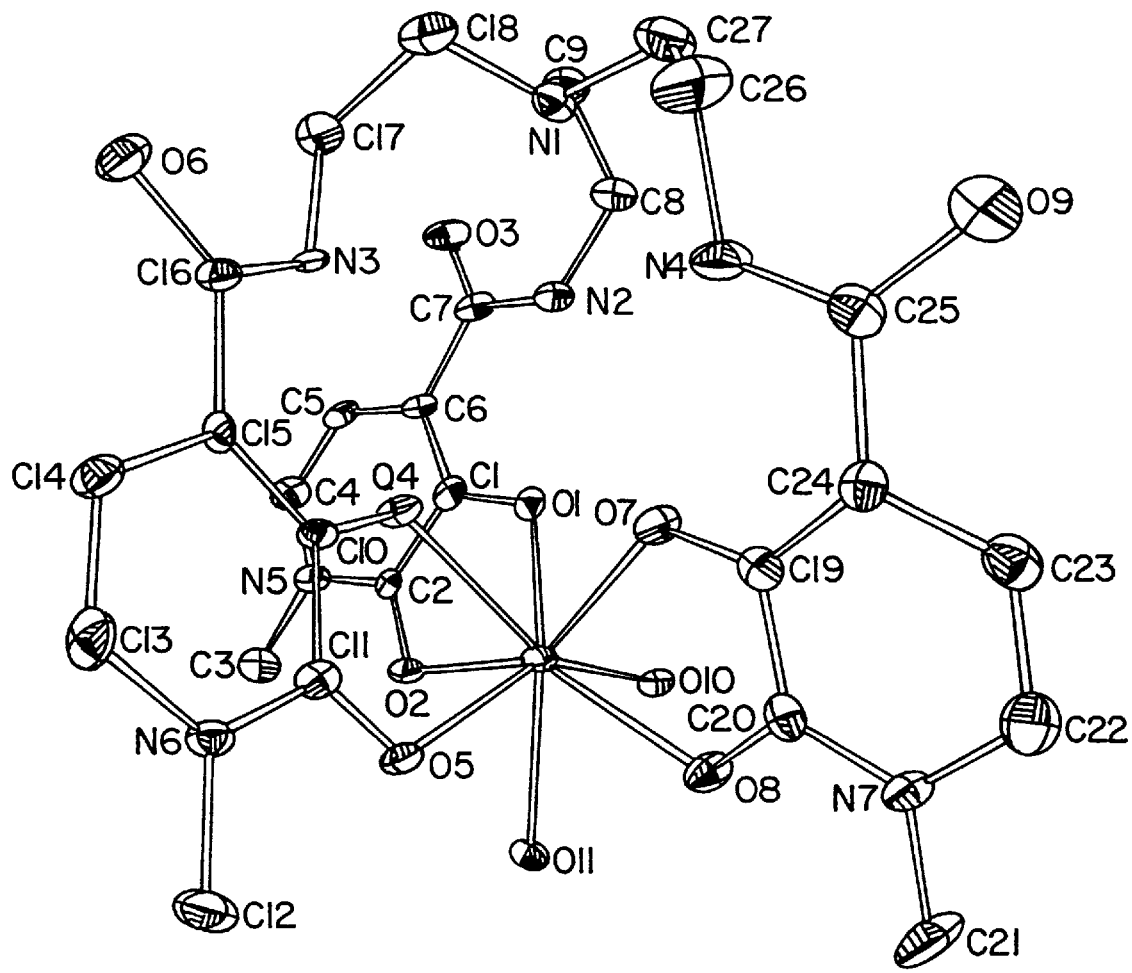
FIG. 2 is a diagram showing crystal structure of the Gd(III)-TREN-3,2-HOPO complex.

Crystals of this compound suitable for x-ray diffraction are prepared by vapor diffusion of ether into its wet DMF solution. Its chemical formula is $GdC_{29}H_{30}N_7O_9 \cdot 2H_2O \cdot C_3H_7NO$. Its crystal structure is shown in FIG. 2 and the crystallographic data and parameters for this compound are shown in Table 2.

Solution of the structure indicates that the compound consists of molecules containing one gadolinium (III) ion which coordinates with a hexadentate TREN-Me-3,2-HOPO ligand and two water molecules, so that the square antiprism coordination requirement of the gadolinium atom is satisfied by the oxygen atoms of three bidentate hydroxypyridonate moieties and two water molecules. The structure reveals extensive delocalization and a strong hydrogen bonding between the amide proton and its adjacent HOPO oxygen donor, as shown in Formula 8. Because of the large number of coordinated water molecules, this class of compounds is expected to show good nuclear magnetic relaxation properties as need for magnetic resonance imaging.

TABLE 2

Crystallographic Data and Parameters for
$GdO_9N_7C_{27}H_{30} \cdot 2H_2O \cdot C_3H_7NO$

| Formula: | $GdO_9N_7C_{27}H_{30} \cdot 2H_2O \cdot C_3H_7NO$ |
|---|---|
| Formula Weight (amu) | 862.96 |
| Temperature (°C.) | −117 |
| Crystal System | triclinic |
| Space Group (#) | P1 (#2) |
| Cell Constants[a] | |
| a (Å) | 10.791(3) |
| b (Å) | 12.901(4) |
| c (Å) | 13.566(4) |
| α (°) | 85.42(2) |
| β (°) | 67.38(2) |
| γ (°) | 74.58(2) |
| Z | 2 |
| V (Å³) | 1680(1) |
| Abs. Coeff., $\mu_{calc}$ (cm⁻¹) | 20.54 |
| $d_{calc}$ | 1.706 |
| F (000) | 874 |
| Crystal dimensions (mm) | 0.30 × 0.110 × 0.08 mm |
| Radiation | Mo—Ka (λ = 0.71073) |
| Diffractometer | Enraf-Nonius CAD-4 |
| h, k, l range collected | 0→11, −13→+13, −14→+14 |
| 2θ range | 3–45° |
| Scan Type | Omega-2Theta |
| Scan speed (θ, °/min.) | 5.49°/min |
| Reflections collected | 4377 |
| Unique reflections: | 4377 |
| Reflections with ($F_o^2 > 3*\sigma(F_o^2)$) | 3576 |
| Number of parameters | 460 |
| Data/parameter ratio | 7.8 |
| R = [Σ\|ΔF\|/Σ\|$F_0$\|] | 0.036 |
| $R_w = [\Sigma w(\Delta F)^2/\Sigma w F_o^2]$ | 0.039 |
| GOF | 1.385 |
| Final Diff. $\rho_{max}$ (e⁻/Å³) | +1.008[b] |

[a] unit cell parameters and their esd's were derived by a least-squares fitting of the setting angles of 24 reflections in the range 23.24° ≤ 2θ ≤ 24–56°.
[b] Located near Gd.

Example 21

In Vivo Test of Promoting Excretion of $^{238}$Pu(IV) in Mice by Injected Ligands The novel chelating agents of the present invention were tested for their effectiveness in promoting excretion of $^{238}$Pu(IV) in mice by injected ligands as follows. Mice, in groups of five, each received an intravenous injection of 1850 Bq $^{238}$Pu(IV) in 0.2 mL of citrate buffer. One hour later, 30 μmol/kg of ligand was injected intraperitoneally in 0.5 mL of saline. The mice were killed 24 hours after the Pu injection, frozen, and dissected after partial thawing. The $^{238}$Pu in skeleton, soft tissues, and separated excreta was determined by counting the $^{234}$U L x-rays. Results of removal of $^{238}$Pu(IV) from mice by injected ligands are summarized in Table 3, which also includes data for CaNa₃-DTPA and other reference ligands and the Pu-injected controls. As illustrated by the data in Table 3, all the novel 3,2-HOPO chelating agents provide effective Pu removal, and the tetradentate ligands such as 5-LI-0-Me-3,2-HOPO, 5-LI-Me-3,2-HOPO and 4-LI-Me-3,2-HOPO are, surprisingly, as effective or more effective than the hexadentate and octadentate chelating agents. While in the case of multidentate 1,2-HOPO and catechoylamide chelating agents, octadentates are always better chelating agents than the correspond hexadentates and tetradentates.

groups of five, each received an intravenous injection of 1850 Bq $^{238}$Pu(IV) in 0.2 M]L of citrate buffer. Three minutes later, 30 μmol/kg of ligand was given by gavage in 0.5 ml of saline. The mice were killed 24 hours after the $^{238}$Pu(IV) injection, frozen, and dissected after partial thawing. The $^{238}$Pu(IV) in skeleton, soft tissues, and separated excreta was determined by counting the $^{234}$U L x-rays. Results of removal of $^{238}$Pu(IV) from mice by orally admin-

TABLE 3

Removal of $^{238}$Pu(IV) from Mice by Injected Ligands Composed of Me-3,2-HOPO

| Ligand | no. of mice | percent of injected $^{238}$Pu ± SD at 24 h[a,b] | | | | | excreta | |
|---|---|---|---|---|---|---|---|---|
| | | tissues | | | | | feces and GI contents | urine 0–24 h |
| | | skeleton | liver | soft tissue | kidneys | whole body | | |
| Me-3,2-HOPO Ligands[c] | | | | | | | | |
| 5-LI—O—Me-3,2-HOPO | 5 | 11 ± 1.6 | 2.1 ± 0.3[d] | 1.6 ± 0.2[d] | 0.2 | 15 ± 2.1[d] | 61.7 | 23.5 |
| 5-LI—Me-3,2-HOPO | 10 | 10 ± 1.2 | 3.1 ± 0.8[d] | 1.9 ± 0.5 | 0.3 | 16 ± 1.9[d] | 67.6 | 17.5 |
| 4-LI—Me-3,2-HOPO | 10 | 11 ± 1.7 | 3.7 ± 1.5[d] | 1.9 ± 0.5 | 0.4 | 17 ± 2.7[d] | 63 | 19.4 |
| TREN—Me-3,2-HOPO | 15 | 10 ± 1.1 | 5.0 ± 2.2[d] | 2.5 ± 0.8 | 0.6 | 18 ± 2.7[d] | 43.3 | 37 |
| H(2,2)-Me-3,2-HOPO | 10 | 11 ± 1.7 | 3.8 ± 1.1[d] | 2.8 ± 1.6 | 1.3 | 19 ± 2.9[d] | 45.3 | 36 |
| ME—Me—3,2-HOPO | 5 | 12 ± 1.8 | 6.1 ± 4.9[d] | 3.0 ± 2.0 | 0.9 | 22 ± 8.5[d] | 70.1 | 33.5 |
| 6-LI—Me-3,2-HOPO | 10 | 12 ± 1.8 | 6.5 ± 3.7[d] | 3.7 ± 1.8 | 0.5 | 23 ± 4.9[d] | 62.9 | 14.4 |
| 3-LI—Me-3,2-HOPO | 10 | 14 ± 1.9 | 9.5 ± 4.9[d] | 2.6 ± 0.4 | 0.5 | 27 ± 5.2 | 41.6 | 32 |
| H(3,2)-Me-3,2-HOPO | 5 | 10 ± 2.0 | 14 ± 6.1 | 2.4 ± 0.3[d] | 1.2 | 28 ± 4.8 | 52.1 | 19.5 |
| TREN-bis(Me-3,2-HOPO)-bis acetic acid | 10 | 20 ± 1.7 | 6.6 ± 2.2[d] | 2,6 ± 0.8 | 0.5 | 30 ± 3.6 | 34.6 | 8.7 |
| TRPN—Me-3,2-HOPO | 5 | 14 ± 3.2 | 17 ± 5.0 | 2.0 ± 1.1 | 0.7 | 33 ± e5.3 | 11.5 | 55 |
| H(4,2)-Me-3,2-HOPO | 5 | 12 ± 2.9 | 29 ± 6.1 | 1.9 ± 1.0 | 1.8 | 46 ± 8.5 | 26.8 | 28 |
| DFO—Me-3,2-HOPO[e] | 10 | 17 ± 2.4 | 13 ± 3.5 | 19 ± 3.0 | 3.0 | 53 ± 3.4 | 26.4 | 21 |
| Reference Ligands[c,e] | | | | | | | | |
| DFO-(1,2-HOPO) | 5 | 6.0 ± 0.5[d] | 5.1 ± 2.2[d] | 2.3 ± 0.5[d] | 0.1 | 13 ± 2.9[d] | 46.7 | 9.5 |
| 3,4,3-LI(1,2-HOPO) | 5 | 7.5 ± 0.7[d] | 8.9 ± 1.7[d] | 1.6 ± 0.6[d] | 0.2 | 18 ± 1.7[d] | 57 | 23 |
| CaNa$_3$-DTPA | 15 | 12 ± 2.3 | 17 ± 4.0 | 3.5 ± 1.6 | 1.1 | 33 ± 6.6 | 5.1 | 61 |
| 3,4-LI(1,2-HOPO) | 5 | 9.9 ± 3.6 | 18 ± 4.8 | 5.8 ± 1.3 | 0.6 | 34 ± 9.2 | 58 | 7.9 |
| 3-LI(1,2-HOPO) | 5 | 17 ± 2.8 | 8.7 ± 1.2[d] | 11 ± 0.8 | 1.4 | 38 ± 4.4 | 53.3 | 8.7 |
| DFO | 10 | 20 ± 11 | 19 ± 13 | 4.5 ± 1.4 | 1.8 | 45 ± 2.5 | 15.1 | 38 |
| ME-(1,2-HOPO) | 5 | 17 ± 2.5 | 18 ± 6.3[d] | 10 ± 1.8 | 1.8 | 47 ± 9.4 | 43 | 9.6 |
| Pu-Injected Controls (fed) | | | | | | | | |
| kill at 24 h | 143 | 31 ± k7.4 | 50 ± 7.9[d] | 7.8 ± 2.1 | 1.8 | 91 ± 6.0 | 4.4 | 3.8 |

[a]SD = [Σdev$^2$(n − 1)$^{-1}$]$^{1/2}$. No SD is shown for kidneys or excreta, because samples for five-mouse groups were pooled for radioanalysis. Data for each mouse, expressed as % ID, were normalized to 100% material recovery; discrepancies are due to rounding.
[b]Ligands were injected (30 μmol kg$^{-1}$, i.p.) at 1 h, and mice were killed at 24 h after iv injection of $^{238}$Pu(IV) citrate.
[c]Skeleton, liver, and body Pu of ligand-treated groups are significantly less than 24 h Pu-injected controls (t test, p ≤ 0.01).
[d]Significantly different from mice given CaNa$_3$-DTPA (t test, p ≤ 0.01).
[e]Reported previously and shown here to facilitate comparisons.

Example 22

In Vivo Test of Promoting Excretion of $^{238}$Pu(IV) in Mice by Orally Administered Ligands The novel chelating agents of the present invention were tested for their effectiveness in promoting excretion of $^{238}$Pu(IV) by oral administration to mice as follows. Mice in istered ligands are summarized in Table 4, which also includes data for the reference ligands, and the Pu-injected controls. As illustrated by the data in Table 4, the octadentate and hexadentate chelating agents are superior by oral administration, and the hexadentate ligand TREN-Me-3,2-HOPO is the most effective both (by oral and injection) cases.

TABLE 4

Removal of $^{238}$Pu(IV) from Mice by Orally Administered Ligands Composed of Me-3,2-HOPO

| Ligand | no. of mice | percent of administered $^{238}$Pu ± SD at 24 h[a,b] | | | | | excreta feces and GI contents | urine 0–24 h |
|---|---|---|---|---|---|---|---|---|
| | | skeleton | liver | soft tissue | kidneys | whole body | | |
| Me-3,2-HOPO Ligands | | | | | | | | |
| H(2,2)-Me-3,2-HOPO | 15 | 11 ± 4.6 | 7.6 ± 6.5 | 4.0 ± 2.1[c] | 0.4 | 23 ± 11 | 37.9 | 39 |
| TREN—Me-3,2-HOPO | 10 | 13 ± 5.5 | 8.5 ± 4.7 | 1.9 ± 1.2[c] | 0.7 | 25 ± 12 | 34.1 | 42 |
| H(3,2)-Me-3,2-HOPO | 5 | 14 ± 6.7 | 13 ± 5.9 | 4/1 ± 1.9 | 1.4 | 33 ± 13 | 25.4 | 42 |
| H(4,2)-Me-3,2-HOPO | 5 | 15 ± 6.2 | 19 ± 4.9 | 1.8 ± 0.8 | 1.3 | 37 ± 10 | 10.1 | 52.4 |
| 5-LI—O—Me-3,2-HOPO | 5 | 23 ± 5.9 | 16 ± 4.4 | 4.0 ± 0.8[c] | 0.8 | 43 ± 10 | 44.7 | 12.5 |
| 5-LI—Me-3,2-HOPO | 5 | 23 ± 11 | 24 ± 5.3 | 4.4 ± 2.0 | 0.8 | 53 ± 17 | 27.1 | 20 |
| 4-LI—Me-3,2-HOPO | 5 | 15 ± 6.1 | 34 ± 7.7 | 3.6 ± 1.5 | 0.5 | 54 ± 13 | 13.6 | 32.5 |
| DFO—Me-3,2-HOPO) | 10 | 20 ± 7.6 | 22 ± 7.7 | 15 ± 4.0 | 2.4 | 60 ± 11 | 17.3 | 22.4 |
| TRPN—Me-3,2-HOPO | 5 | 28 ± 8.0 | 28 ± 3.1 | 4.3 ± 1.7[c] | 0.7 | 60 ± 11 | 7.9 | 27 |
| 3-LI—Me-3,2-HOPO | 10 | 27 ± 7.7[c] | 33 ± 4.4 | 5.0 ± 1.2 | 0.8 | 66 ± 11 | 7.9 | 27 |
| TREN-bis(Me-3-2-HOPO)bis acetic acid | 10 | 28 ± 5.2[c] | 38 ± 2.7[d] | 4.1 ± 0.7 | 0.6 | 71 ± 5.6 | 10.0 | 19.1 |
| 6-LI—Me-3,2-HOPO | 10 | 25 ± 3.1[c] | 44 ± 5.0 | 6.2 ± 1.1 | 1.3 | 76 ± 5.8[c] | 9.8 | 14.2 |
| ME—Me-3,2-HOPO | 5 | 34 ± 24.5 | 40 ± 1.8 | 7.5 ± 1.7 | 1.2 | 82 ± 3.9[c] | 6.7 | 12.4 |
| Reference Ligands[c] | | | | | | | | |
| DFO-(1,2-HOPO) | 5 | 12 ± 2.4 | 11 ± 4.9 | 1.3 ± 0.7 | 0.1 | 24 ± 7.7 | 51.4 | 25.7 |
| 3,4-,3-LI(1,2-HOPO) | 5 | 33 ± 5.0 | 22 ± 7.7[d] | 3.9 ± 0.8 | 0.2 | 60 ± 8.2 | 5.0 | 9.5 |
| Pu-Injected Controls (fed) | | | | | | | | |
| kill at 24 h | 20 | 39 ± 7.2 | 43 ± 6.2[d] | 6.0 ± 1.5 | 1.6 | 90 ± 3.6 | 4.5 | 5.4 |

[a]SD = $(\Sigma \text{dev}^2(n - 1)^{-1})^{1/2}$. No SD is shown for kidneys or excreta, because samples for five-mouse groups were pooled for radioanalysis. Data for each mouse, expressed as % ID, were normalized to 100% material recovery; discrepancies are due to rounding.
[b]Ligands were given (30 μmole kg$^{-1}$, by gavage) at 3 min, and mice were killed at 24 h after iv injection of $^{238}$Pu(IV) citrate.
[c]Mean is significantly less than that of 24 h fasted Pu controls (t test, p $\leq$ 0.01)
[d]Mean is significantly less than that of mice gavaged with CaNa$_3$-DTPA (t test, p $\leq$ 0.01)

Example 23

In Vivo Test of Promoting Excretion of Am(III), Np(IV), and U(VI) in Mice by Injected TREN-Me-3,2-HOPO One of the novel chelating agents of the present invention, TREN-Me-3,2-HOPO, was also tested for effectiveness in promoting excretion of $^{241}$AM(III), $^{237}$Np(V), and $^{232}$U(VI) by injection into mice, as follows: Mice, in groups of five, each received an intravenous injection of (a) 1100 Bq of $^{241}$Am(III) in 0.2 mL of citrate buffer, (b) 150 Bq of $^{232}$UO$_2$Cl$_2$ plus 3.6 mg of $^{235}$UO$_2$Cl$_2$ in 0.2 mL of saline, or (c) 200 Bq of $^{237}$NpO$_2$Cl (7.5 Mg of $^{237}$NPO$_2$Cl) in 0.2 mL of saline. Three to five minutes later, 30 μmol/kg of TREN-Me-3,2-HOPO was injected intraperitoneally in 0.5 mL of saline. The mice were killed 24 hours after the actinide injection, frozen, and dissected after partial thawing. The skeleton, soft tissues, and separated excreta were radioanalyzed by counting the $^{241}$Am gamma rays, or the alpha particles emitted by $^{237}$Np or $^{232}$U (and its ingrowing daughters). Removal of those actinides from mice by injected TREN-Me-3,2-HOPO is summarized in Table 5, which also includes data for mice similarly treated with CaNa$_3$-DTPA and for actinide-injected controls. As shown by the data in Table 5, TREN-Me-3,2-HOPO reduced the body content of all three actinides to a significantly greater degree than CaNa$_3$-DTPA. Compared with controls, the Am content of all tissues was greatly reduced, the Np content of the soft tissues was significantly reduced, and more than one-half of the U burden in the kidneys was removed. The structure of Am(III)-TREN-Me-3,2-HOPO is considered to resemble that of the Gd(III) complexes (see Example 20). Complexation of the fraction of Np(V) that is reduced in vivo to Np(IV) is considered to resemble that of Pu(IV). Complexation of U(VI) is considered to take place through binding to UO$_2^{2+}$.

TABLE 5

Removal of $^{241}$Am(III), $^{237}$Np(V), or $^{232,234,234}$U(VI) from Mice by Orally Injected TREN—Me-3,2-HOPO[a]

| Ligand | percent of injected actinide ± SD at 24 h[a,b,c] | | | | | excreta feces and GI contents | urine 0–24 h |
|---|---|---|---|---|---|---|---|
| | tissues | | | | whole | | |
| | skeleton | liver | soft tissue | kidneys | body | | |
| Am (III) | | | | | | | |
| TREN—Me-3,2-HOPO | 8.1 ± 6[d] | 1.0 ± 0.6[d,e] | 1.6 ± 0.6[d] | 0.2 | 11 ± 1.4[d,e] | 8 | 51 |
| CaNa$^3$—DTPA | 8.5 ± 0.9[d] | 13 ± 1.5[d] | 1.9 ± 0.3[d] | 0.4 | 24 ± 1.3[d] | 8.0 | 68 |
| Am controls, kill 24 | 27 ± 5.3 | 50 ± 5.3 | 5.7 ± 0.7 | 1.2 | 84 ± 3.7 | 2.6 | 14 |
| Np (V) | | | | | | | |
| TREN—Me-3,2-HOPO | 34 ± 4.5 | 3.8 ± 5.7[d,e] | 3.1 ± 1.1 | 1.0 | 42 ± 11[d,e] | 17 | 40 |
| CaNa$_3$—DTPA | 40 ± 4.4 | 14 ± 5.7 | 3.5 ± 0.9 | 1.3 | 58 ± 8.0 | 1.5 | 40 |
| Np controls, kill 24 h | 37 ± 5.1 | 1.4 ± 2.3 | 5.8 ± 2.3 | 1.7 | 59 ± 4.1 | 41[f] | |
| U (VI) | | | | | | | |
| TREN—Me-3,2-HOPO | 16 ± 2.4 | 0.6 ± 0.3 | 1.6 ± 0.3 | 1.6 ± 0.3 | 9.4 ± 6.0[d,e] | 2.3 | 70 |
| CaNa$_3$-DTPA | 19 ± 3.0 | 1.0[c] | 2.2 ± 0.,1 | 17 ± 2.8 | 38 ± 0.7 | 62[f] | |
| U controls, kill 24 | 17 ± 2.5 | 1.4[c] | 2.8 ± 0.5 | 19 ± 6.9 | 40 ± 7.8 | 60[f] | |

[a]Ligands (30 μmol/kg) i.p. at 3 to 5 min after actinide i.v.; kill at 24 h.
[b]Groups of five mice except: TREN—Me-3,2-HOPO i.p. at 3 min after 24 h Am, 10; 24 h Am, Np, or U controls, 10. Results are expressed as percent of injected actinide (ID %) normalized to 100% material recovery; discrepancies are due to rounding.
[c]Standard deviation, SD = [Σdev$^2$(n − 1)$^{-1}$]$^{1/2}$. Kidneys of Am- and Np-injected mice, livers of some U-injected groups, and all excreta were pooled for each five-mouse groups.
[d]Significantly less actinide than appropriate controls (t test, p ≤ 0.01).
[e]Significantly improved actinide reduction than for mice given CaNa$_3$-DTPA in same protocol.
[f]Combined excreta.

Example 24

In Vivo Toxicity Test of Injected Ligands in Mice

The test of acute toxicity of these novel ligands was carried out as follows. Groups of five mice were each given a single i.p. injection of 100 μmol/kg of ligand a day for 10 days or given two i.p. injections of 500 μmol/kg in 8 hours. The ligand was dissolved in 0.5 to 1.0 ml of saline at pH 7 to 8. After a period of observation, the mice were killed, selected tissues were removed and fixed for histopathological examination, and unusual findings at autopsy were recorded. Results of the initial test of toxicity of the ligands tested are summarized in Table 6. The highly effective ligands, such as TREN-Me-3,2-HOPO, 5-LI-Me-3,2-HOPO and 5-LI-O-Me-3,2-HOPO proved to be of low toxicity, even at the relatively high dosage of 2×500 μmol/kg in 8 hours.

TABLE 6

Initial Evaluation of Acute Toxicity in Mice of Ligands Composed of 1-Me-3,2-HOPO[a]

| protocol and ligand | study length (d)[b] | no. of mice | no. of survivors[c] | percent control mean ± SD[d] | | |
|---|---|---|---|---|---|---|
| | | | | body weight | kidney weight | plasma urea N |
| I. 100 μmol · kg − 1 × 10 daily | | | | | | |
| TREN—Me-3,2-HOPO | 11 | 5 | 5 | 102 ± 1 | — | 112 ± 10 |
| TERN—Me-3,2-HOPO | 21 | 5 | 5 | 106 ± 4 | — | 120 ± 9 |
| H(2,2-Me-3,2,-HOPO | 11 | 5 | 5 | 92 ± 6 | — | 223 ± 28 |
| H(2,2-Me-3,2-HOPO | 21 | 5 | 5 | 87 ± 9 | — | 225 ± 188 |
| 5-LI—Me-3,2-HOPO | 11 | 5 | 5 | 102 ± 5 | 109 ± 14 | 89 ± 1 |
| 5-LI—Me-3,2-HOPO | 21 | 5 | 5 | 102 ± 5 | 100 ± 4 | 101 ± 2 |

TABLE 6-continued

Initial Evaluation of Acute Toxicity in Mice of Ligands Composed of 1-Me-3,2-HOPO[a]

| protocol and ligand | study length (d)[b] | no. of mice | no. of survivors[c] | percent control mean ± SD[d] | | |
|---|---|---|---|---|---|---|
| | | | | body weight | kidney weight | plasma urea N |
| 5 LI—O—Me-3,2-HOPO | 11 | 5 | 5 | 103 ± 5e | 100 ± 19 | 83 ± 5 |
| 5-LI—O—Me-3,2-HOPO | 21 | 5 | 5 | 101 ± 5 | 111 ± 5 | 86 ± 18 |
| IA. 100 μmol · kg$^{-1}$ × 2 daily | | | | | | |
| 3-LI—Me-3,2-HOPO | 6 | 10 | 0 | 89 ± 4 | 222 ± 29 | >1800 |
| 6-LI—Me-3,2-HOPO | 3 | 5 | 5 | 83 ± 3 | 132 ± 11 | 343 ± 140 |
| 6-LI—Me-3,2-HOPO | 11 | 5 | 3 | 101 ± 5 | 112 ± 13 | 92 ± 6 |
| IB. 100 μmol · kg$^{-1}$ | | | | | | |
| 4-LI—(Me-3,2-HOPO | 5 | 3 | 0 | 85 ± 8 | 190 ± 63 | >2000 |
| II. 500 μmol · kg$^{1}$ × 2 in 8 h | | | | | | |
| TREN—(Me-3,2-HOPO | 8 | 19 | 19 | 101 ± 4 | — | 119 ± 15 |
| H(2,2)-Me-3,2-HOPO | 8 | 10 | 3 | 94 ± 6 | — | 169 ± 10 |
| 5-LI—Me-3,2-HOPO | 11 | 5 | 5 | 99 ± 3 | 109 ± 9 | 98 ± 18 |
| 5-LI—O—Me-3,2-HOPO | 11 | 10 | 110 | 100 ± 2 | 108 ± 10 | 77 ± 10 |

[a]Control data: Body weight ratio, (W(t)/W(o)) 8 to 11 d, 1.01 ± 0.03 (15); 21 d, 1.06 ± 0.06 (10). Kidney weight (g), 2 × left kidney, 0.44 ± 0.04 (25). Plasma urea N (mg dL$^{-1}$) (15 groups of five) range 11.4 ± 1.2 to 22.2 ± 2.5, median 20.2 ± 2.3, grand mean 15 groups 18.5 ± 3.2.
[b]Days after first ligand injection.
[c]Number of survivors and of autopsied mice contributing numerical data, with two exceptions. In the case of 3-LI-Me-3,2-HOPO data are shown for two moribund mice autopsied on d 3; all mice were dead by d 3. In all cases mice found dead were not autopsied.
[d]Underlined means significantly different from control means, t test, p >0.01.
[e]Two replicate 10-mouse groups, one mouse lost in an injection accident.

Example 25

Synthesis and Initial Evaluation of Water-Soluble 3, 2-HOPO Chelating Polymer

Synthesis:

To a solution of 1.7 g commercially available water-soluble polyamine polymer PEI (polyethyleneimine, with average molecular weight of 30K Dalton) in dry DMF (50 mL), 3.60 g of Me-3,2-HOPO thiazolide (Formula 24 with $R_1$=methyl) was added. The solution was stirred at room temperature for 24 hours. The solvent was then removed and the residue was dissolved in 50 mL water containing 1 mL of pure acetic acid. The aqueous solution was extracted three times with methylene chloride to remove byproducts and impurities, and then evaporated to dryness. The residue was dissolved in 20 mL of a 1:1 mixture of glacial acetic acid and hydrochloric acid (37%). The resulting mixture was stirred at room temperature for two days and evaporated to dryness, with a yield of 85–90%.

Initial Extraction Evaluation:

Extractions were performed with the radioactive isotopes $^{241}$Am and 238Pu at the Los Alamos National Laboratory. The actinides were in nitric acid solution. The chelating polymer solution was adjusted with dilute HNO$_3$ or dilute NaOH to obtain two separate pH values, pH 2 and pH 3. After adjusting the pH, the solutions were shaken for thirty minutes, placed in an ultrafiltration unit with 10,000 MWCO and centrifuged. The unit was weighed both before and after each centrifugation. The retentate and permeate were poured into separate vials, each with liquid scintillation cocktail, and the respective unit was also placed in the vials. The vials were counted by liquid scintillation counting. Initial results indicated that the water-soluble chelating polymer had a strong affinity for the actinides. The average log $K_d$ for $^{241}$Am(III) was 4.3 at pH 2 and 5.5 at pH 3, and the average log $K_d$ for $^{238}$Pu(VI) was 4.6 at pH 2 and 5.2 at pH 3, where the $K_d$ is the distribution constant for the distribution of the actinides between the chelating polymer and the water phases.

Example 26

Synthesis of 3,2-HOPO Chelating Polystyrene Polymers

The 3,2-HOPO chelating polystyrene polymers were synthesized from a propylamine or dien resin in which 1,3-propyldiamine or diethylenetriamine (dien) is linked to the polystyrene resin uniquely through the amino nitrogen. To a slurry of the resin in dioxane, equal molar amounts of Me-3,2-HOPO thiazolide (Formula 24 with $R_1$=methyl) and triethylamine were added for the amount of amine in the resin. The slurry was stirred at room temperature for 24 hours. The functionalized resin was then filtered, washed with dioxane and dried. The resin was then deprotected with a 1:1 mixture of glacial acetic acid and hydrochloric acid (37%) at room temperature for two days, and washed thoroughly with water and methanol in succession. Initial tests indicated that this polystyrene-based 3,2-HOPO resin uptake was 99% Pu(VI) from Pu(VI)-0.1M HNO$_3$ solution. The tests were carried out with the radioactive plutonium isotope $^{242}$Pu at the Lawrence Livermore National Laboratory's Glenn T. Seaborg Institute for Transactinium Science, Livermore, Calif.

Example 27

Liquid/Liquid Extraction of Plutonium From Aqueous Solution

Liquid/liquid extractions were performed with the radioactive plutonium isotope $^{242}$Pu at the Lawrence Livermore National Laboratory's Glenn T. Seaborg Institute for Transactinium Science, Livermore, Calif. The aqueous phase contained $^{242}$Pu, while the organic phases contained 3,2-HOPO ligands at 2–5 mM concentration. Kinetic studies were the primary method used to determine the efficacy of the specific ligand in organic solvent. Generally, five microcentrifuge tubes were prepared with the same organic and aqueous phases, and shaken with a vortex-style mixer for 1, 5, 10, and 20 minutes. After mixing, an aliquot of each phase was pipetted from the tube into a scintillation vial, mixed with a scintillation cocktail, and scintillation counted to determine the amount of the radioactive species present in each phase after extraction.

Two representative compounds, Me-3,2-HOPO-octylamide (Formula 9C: R=octyl; R'=H; $R_1$=methyl) and Me-3,2-HOPO-decylamide (Formula 9C: R=decyl; R'=H; $R_1$=methyl), were used for the initial test.

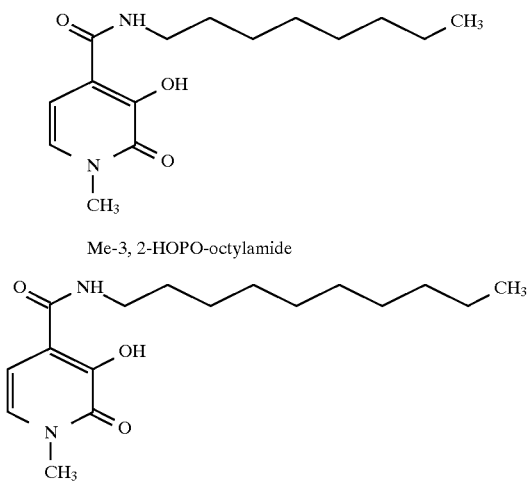

Me-3, 2-HOPO-octylamide

Table 7 shows the results of Pu(IV) extraction with Me-3, 2-HOPO-octylamide using both an octanol/water and methylisobutylketone (MIBK)/water system, while Table 8 shows the results obtained with Me-3,2-HOPO-decylamide, using the same two systems.

TABLE 7

Pu(IV) Extraction Data for Me-2-HOPO-Decylamide

| Organic Phase | Pu(IV) Ion Strength in Aqueous Phase | Extraction Time (min) | % Pu(IV) Extracted[a] | Partition Coefficient[b] | Decontamination Factor[c] |
|---|---|---|---|---|---|
| Octanol | 5.0M | 1.0 | 98.3 ± 4.6 | 56.64 ± 1.58 | 57.64 ± 0.84 |
| | | 5.0 | 96.4 ± 4.5 | 26.98 ± 1.13 | 27.98 ± 0.25 |
| | | 10.0 | 93.6 ± 4.4 | 14.74 ± 0.83 | 15.74 ± 0.47 |
| | | 20.0 | 88.3 ± 4.1 | 7.51 ± 0.53 | 8.51 ± 0.31 |
| | 0.10M | 1.0 | 68.9 ± 3.3 | 2.22 ± 0.19 | 3.22 ± 0.15 |
| | | 5.0 | 96.2 ± 4.5 | 25.39 ± 1.12 | 26.39 ± 0.61 |
| | | 10.0 | 95.2 ± 4.4 | 19.71 ± 1.00 | 20.71 ± 0.55 |
| | | 20.0 | 92.4 ± 4.3 | 12.11 ± 0.75 | 13.11 ± 0.42 |

TABLE 7-continued

Pu(IV) Extraction Data for Me-2-HOPO-Decylamide

| Organic Phase | Pu(IV) Ion Strength in Aqueous Phase | Extraction Time (min) | % Pu(IV) Extracted[a] | Partition Coefficient[b] | Decontamination Factor[c] |
|---|---|---|---|---|---|
| MIBK | 5.0M | 1.0 | 97.9 ± 4.5 | 46.00 ± 1.48 | 47.00 ± 0.79 |
| | | 5.0 | 97.9 ± 4.5 | 46.62 ± 1.43 | 47.62 ± 0.76 |
| | | 10.0 | 95.8 ± 4.4 | 22.87 ± 1.07 | 23.87 ± 0.58 |
| | | 20.0 | 81.9 ± 3.8 | 4.52 ± 0.35 | 5.52 ± 0.23 |
| | 0.10M | 1.0 | 98.2 ± 4.5 | 53.63 ± 1.60 | 54.63 ± 0.85 |
| | | 5.0 | 95.9 ± 4.4 | 23.40 ± 1.14 | 24.40 ± 0.62 |
| | | 10.0 | 97.7 ± 4.5 | 42.43 ± 1.43 | 14.63 ± 0.46 |
| | | 20.0 | 93.2 ± 4.3 | 13.63 ± 0.82 | 6.97 ± 0.27 |

[a]% Pu(IV) Extracted = $[A_{org}/A_{org+aq}] \times 100$, where $A_{org}$ is the radioactivity of the organic phase and $A_{org+aq}$ is the total radioactivity, i.e., the experimentally determined total radioactivity instead of the theoretical total radioactivity
[b]The partition coefficient is the distribution ratio $D = A_{org}/A_{aq}$, where $A_{aq}$ is the radioactivity of the aqueous phase
[c]The decontamination factor is the calculated value $A_{org+aq}/A_{aq}$

TABLE 8

Pu(IV) Extraction Data for Me-2-HOPO-Octylamide

| Organic Phase | Pu(IV) Ion Strength in Aqueous Phase | Extraction Time (min) | % Pu(IV) Extracted[a] | Partition Coefficient[b] | Decontamination Factor[c] |
|---|---|---|---|---|---|
| Octanol | 5.0M | 1.0 | 97.8 ± 4.1 | 44.22 ± 1.43 | 45.22 ± 0.76 |
| | | 5.0 | 97.4 ± 4.5 | 36.91 ± 1.30 | 37.91 ± 0.70 |
| | | 10.0 | 95.2 ± 4.4 | 19.78 ± 0.98 | 20.78 ± 0.54 |
| | | 20.0 | 91.4 ± 4.3 | 10.69 ± 0.67 | 11.69 ± 0.38 |
| | 0.10M | 1.0 | 94.4 + 4.4 | 16.83 ± 0.89 | 17.83 ± 0.50 |
| | | 5.0 | 94.5 ± 4.5 | 17.10 ± 1.12 | 18.10 ± 0.50 |
| | | 10.0 | 92.1 ± 4.3 | 11.71 ± 0.72 | 12.71 ± 0.41 |
| | | 20.0 | 91.2 ± 4.2 | 10.32 ± 0.67 | 11.32 ± 0.38 |
| MIBK | 5.0M | 1.0 | 98.8 ± 4.6 | 79.22 ± 1.71 | 80.22 ± 0.91 |
| | | 5.0 | 98.2 ± 4.6 | 53.99 ± 1.54 | 54.99 ± 0.82 |
| | | 10.0 | 96.4 ± 4.5 | 26.82 ± 1.18 | 27.82 ± 0.64 |
| | | 20.0 | 83.9 ± 3.9 | 5.20 ± 0.40 | 6.20 ± 0.25 |
| | 0.10M | 1.0 | 95.6 ± 4.4 | 21.90 ± 1.09 | 22.90 ± 0.59 |
| | | 5.0 | 91.8 ± 4.3 | 11.22 ± 0.73 | 12.22 ± 0.41 |
| | | 10.0 | 96.8 ± 4.5 | 30.07 ± 1.26 | 31.07 ± 0.68 |
| | | 20.0 | 96.5 ± 4.5 | 27.56 ± 0.76 | 28.56 ± 0.58 |

[a]% Pu(IV) Extracted = $[A_{org}/A_{org+aq}] \times 100$, where $A_{org}$ is the radioactivity of the organic phase and $A_{org+aq}$ is the total radioactivity, i.e., the experimentally determined total radioactivity instead of the theoretical total radioactivity
[b]The partition coefficient is the distribution ratio $D = A_{org}/A_{aq}$, where $A_{aq}$ is the radioactivity of the aqueous phase
[c]The decontamination factor is the calculated value $A_{org+aq}/A_{aq}$

We claim:

1. A chelating agent having the formula

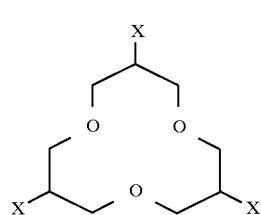

wherein at least one X is

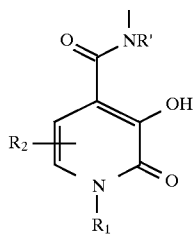

and any remaining X's are independently selected from the group consisting of

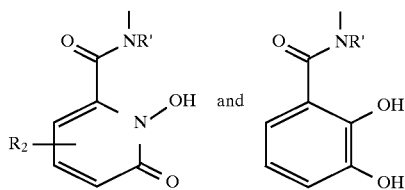

wherein

R$_1$ and R$_2$ are independently selected from the group consisting of hydrogen, C$_1$–C$_4$ aliphatic hydrocarbon groups, and C$_1$–C$_4$ aliphatic hydrocarbon groups substituted by a single halide, hydroxy, carboxy, acrylamido group or aryl group, and R' is a member selected from the group consisting of a hydrogen atom, C$_1$–C$_8$ aliphatic hydrocarbon groups, aryl groups, and C$_1$–C$_8$ aliphatic hydrocarbon groups substituted by amino, carboxy, or hydroxy group.

2. A chelating agent having the formula

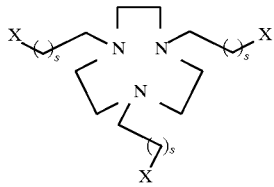

wherein s is 1 or 2, at least one X is

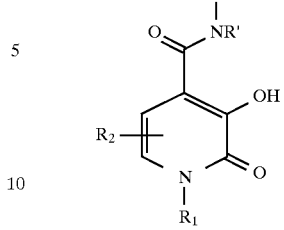

and any remaining X's are independently selected from the group consisting of

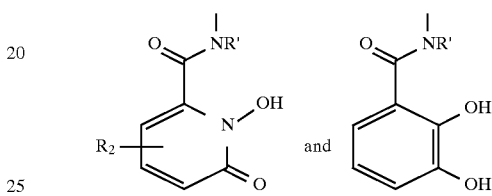

wherein

R$_1$ and R$_2$ are independently selected from the group consisting of hydrogen, C$_1$–C$_4$ aliphatic hydrocarbon groups, and C$_1$–C$_4$ aliphatic hydrocarbon groups substituted by a single halide, hydroxy, carboxy, acrylamido group or aryl group, and R' is a member selected from the group consisting of a hydrogen atom, C$_1$–C$_8$ aliphatic hydrocarbon groups, aryl groups, and C$_1$–C$_8$ aliphatic hydrocarbon groups substituted by amino, carboxy, or hydroxy group.

* * * * *